(12) United States Patent
Takehana et al.

(10) Patent No.: US 10,280,406 B2
(45) Date of Patent: May 7, 2019

(54) MUTANT ENZYME AND PRODUCTION METHOD FOR TERPENOID USING SAID MUTANT ENZYME

(71) Applicant: ADEKA CORPORATION, Tokyo (JP)

(72) Inventors: Toshihiko Takehana, Tokyo (JP); Seiji Koike, Tokyo (JP); Tomohisa Kuzuyama, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 97 days.

(21) Appl. No.: 15/302,903

(22) PCT Filed: Apr. 9, 2015

(86) PCT No.: PCT/JP2015/061168
§ 371 (c)(1),
(2) Date: Dec. 1, 2016

(87) PCT Pub. No.: WO2015/156369
PCT Pub. Date: Oct. 15, 2015

(65) Prior Publication Data
US 2017/0088824 A1   Mar. 30, 2017

(30) Foreign Application Priority Data

Apr. 9, 2014 (JP) ................ 2014-080242

(51) Int. Cl.
C12N 9/04 (2006.01)
C12P 5/00 (2006.01)
C12N 15/52 (2006.01)

(52) U.S. Cl.
CPC ........... *C12N 9/0006* (2013.01); *C12N 15/52* (2013.01); *C12P 5/007* (2013.01); *C12Y 101/01034* (2013.01); *C12Y 101/01088* (2013.01)

(58) Field of Classification Search
None
See application file for complete search history.

(56) References Cited

U.S. PATENT DOCUMENTS

| | | | |
|---|---|---|---|
| 5,116,757 A | 5/1992 | Yamashita et al. | |
| 5,349,126 A | 9/1994 | Chappell et al. | |
| 5,460,949 A | 10/1995 | Saunders et al. | |
| 6,284,506 B1 | 9/2001 | Hoshino et al. | |
| 2003/0054523 A1 | 3/2003 | Hoshino et al. | |
| 2003/0190734 A1 | 10/2003 | Hoshino et al. | |
| 2008/0092829 A1 | 4/2008 | Renninger et al. | |
| 2008/0274523 A1 | 11/2008 | Renninger et al. | |
| 2009/0298150 A1 | 3/2009 | Walker et al. | |
| 2009/0137014 A1 | 5/2009 | Tsuruta et al. | |
| 2010/0037354 A1 | 2/2010 | Karunanandaa et al. | |
| 2011/0124072 A1 | 5/2011 | Walker et al. | |
| 2011/0243969 A1 | 6/2011 | Broeker | |
| 2011/0287476 A1 | 11/2011 | Renninger et al. | |
| 2012/0156249 A1 | 6/2012 | Lang et al. | |
| 2013/0252295 A1 | 9/2013 | Renninger et al. | |
| 2014/0134696 A1 | 5/2014 | Walker et al. | |
| 2015/0024009 A1 | 1/2015 | Lang et al. | |
| 2016/0040190 A1 | 2/2016 | Renninger et al. | |

FOREIGN PATENT DOCUMENTS

| | | |
|---|---|---|
| JP | 3-210174 A | 9/1991 |
| JP | 5-192184 A | 8/1993 |
| JP | 2000-050884 A | 2/2000 |
| JP | 2009-538601 A | 11/2009 |
| JP | 2010-539902 A | 12/2010 |
| JP | 2011-520471 A | 7/2011 |
| JP | 2012-500648 A | 1/2012 |
| JP | 2013-502903 A | 1/2013 |
| JP | 2013-511282 A | 4/2013 |
| WO | 2009-133089 A1 | 5/2009 |
| WO | 2009/143490 A1 | 11/2009 |

OTHER PUBLICATIONS

Written Opinion of the International Searching Authority (English Translation) for International Application No. PCT/JP2015/061168 dated Jul. 7, 2015, 5 pages.
Anonymous: "Chrysemis picta bellii HMGR", Retrieved from the Internet: URL: http://www.uniprot.org/uniparc/UPI000388AA74, dated Aug. 15, 2013 and retrieved on Nov. 8, 2017.
Anonymous: "UPI0003C267EC—Alligator sinensis HMGR", Retrieved from the Internet: URL: http://www.uniprot.org/uniparc/UPI0003C267EC, dated Nov. 7, 2013 and retrieved on Nov. 8, 2017.
Darabi, M., et al., "Study of the 3-hydroxy-3-methylglotaryl-coenzyme A reductase (HMGR) protein in Rosaceae by bioinformatics tools", *Caryologia: International Journal of Cytology, Cytosystematics and Cytogenetics*, vol. 66, No. 4, pp. 351-359 (2013).
Mantzouridou, F., et al., "Observations of squalene accumulation I *Saccharomyces cerevisiae* due to the manipulation of HMG2 and ERG6", *FEMS Yeast Res*, vol. 10, No. 6, pp. 699-707 (2010).
Extended European Search Report for EP Application No. 15776460.6 (International Application No. PCT/JP2015/061168) dated Nov. 20. 2017, 13 pages.

(Continued)

*Primary Examiner* — Kagnew H Gebreyesus
(74) *Attorney, Agent, or Firm* — Heslin Rothenberg Farley & Mesiti P.C.

(57) ABSTRACT

The object of the present invention is to efficiently produce useful terpenoid compounds, and specifically, to provide a method for preparing squalene, which is an important intermediate of terpenoid. The object can be solved by a hydroxymethylglutaryl CoA reductase (HMGR) comprising: (a) an amino acid other than alanine (A) at the 10th position in an $S\alpha 2$ amino acid sequence of HMGR, (b) an amino acid other than proline (P) at the 1st position from the carboxyl terminal in the DKK region of the HMG-CoA binding site of HMGR, (c) an amino acid other than alanine (A) at the 1st position in an $L\alpha 2$ amino acid sequence of HMGR, and (d) an amino acid other than glutamic acid (E) at the 6th position in an $L\alpha 2$ amino acid sequence of HMGR of the present invention.

7 Claims, 9 Drawing Sheets
Specification includes a Sequence Listing.

(56) References Cited

OTHER PUBLICATIONS

Lukacs G et al.: "Cloning of the Rhizomucor miehei 3-hydroxy-3-methylglutaryl-coenzyme A reductase gene and its heterologous expression in Mucor circinelloides", Antonie Van Leeuwenhoek, vol. 95, No. 1, 2009, pp. 55-64, XP055230223, ISSN: 0003-6072.

Wang Y et al.: "Isolation and characterization of a gene encoding 3-hydroxy-3-methylglutary coenzyme A reductase from an endophytic taxol- producing fungus BT2", Ann. Microbiol., vol. 62, No. 2, 2012, pp. 587-595, XP055230225, ISSN: 1590-4261.

Abe Y et al.: "Effect of increased dosage of the ML-236B (compactin) biosynthetic gene cluster on ML-236B production in Penicillium citrinum", Mol. Genet. Genomics, vol. 268, No. 1, 2002, pp. 130-137, XP055230227, ISSN: 1617-4615.

Database genbank Jul. 6, 2010 (Jul. 6, 2010), Jeffries, T.W. et al.: "3-hydroxy-3-methyl-glutaryl coenzyme A reductase (HMG-CoA) [Scheffersomyces stipitis CBS 6054", retrieved from ncbi Database accession No. XP_001385774.

Kuzuyama "Mevalonate and Nonmevalonate Pathways for the Biosynthesis of Isoprene Units" Bioscience, Biotechnology, and Biochemistry, (Japan) 2002, vol. 66, pp. 1691-1627.

Tsunematsu et al. "Engineered Biosynthesis of Natural Products in *Saccharomyces cervisiae*" "Kagaku to Seibutsu", (Japan) 2012, vol. 50, pp. 163-174.

Takahashi et al. "Purification, Characterization, and Cloning of a Eubacterial 3-Hydroxy-3-Methylglutaryl Coenzyme A Reductase, a Key Enzyme Involved in Biosynthesis of Terpenoids" Journal of Bacteriology (U.S.A) 1999, vol. 181, pp. 1256-1263.

Istvan et al. "Crystal structure of the catalytic portion of human I-HMG-CoA reductase: insights into regulation of activity and catalysis" The EMBO Journal (England) 2000, vol. 19, pp. 819-830.

Polakowski et al. "Overexpression of a cytosolic hyroxymethylglutaryl-CoA reductase leads to squalene accumulation in yeast" Applied Microbiology and Biotechnology (1998) 49: pp. 66-71.

International Search Report for International Application No. PCT/JP2015/061168, dated Jul. 7, 2015.

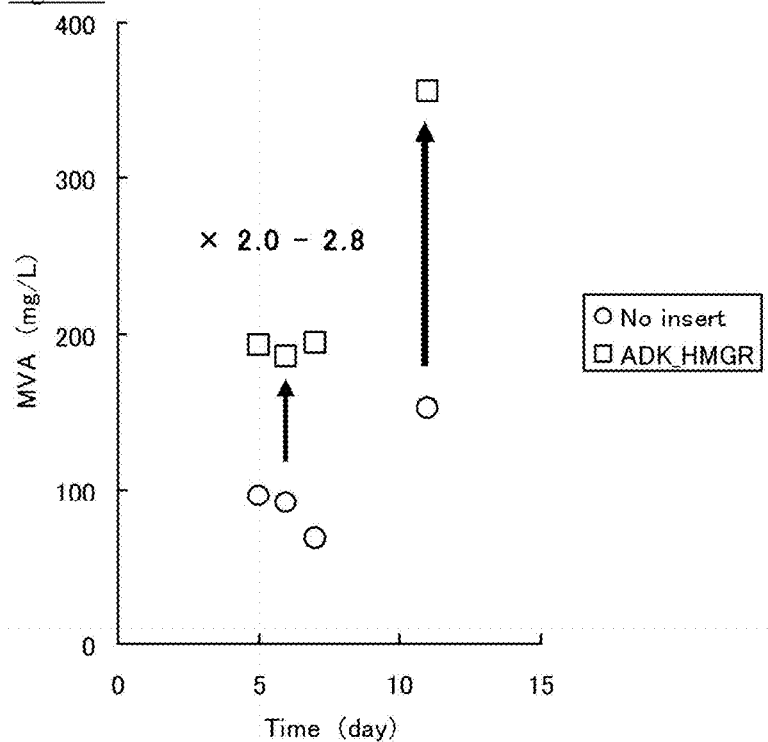

Figure 7-1

```
ADK_HMGR    1  ------MFSLSNYVSNHLASLARLSAHKPIHVIFLTTLTAVAYLSVVCEYLN----FDS---F   51
K7_HMG1     1  MPPLFKGLKQMAKPIAYVSRFSAKRPIHIILFSLIISAFAYLSVIQYYFNGRQLDSNGVF      60
AF273765    1  -----------MLSRLFRMHGLFVASHPHEVIVGTVTLTICMMSMNMFTGMM-----------   41

ADK_HMGR   52  DIS-----------NVSFYHPPSSKDYKDWTLIEDASAYPNAARIAITPLEFRR-IAKHEI   100
K7_HMG1    61  ETAPNKDSNTLFQECSHYYRDSSLDGWVSITAHEASELPAPHHYYLLNLNFNSPNETDSI   120
AF273765   42  ------------------------------------------------------------   41

ADK_HMGR  101  PAIANIFYGVDSTEKYLISEYENAQDSIDSIRTVVSNDGTAMKIVHQYKTSKYQEYLKN-   159
K7_HMG1   121  PELANIVFEKQ-NTKYILQEDLSVSKEIS------STDGTKMRLRSDRKSLFDVKTLAYS   173
AF273765   42  -KICGMNTECP----KFEEDVLS------------------------------------    59

ADK_HMGR  160  AIKTLQSVIRGAETYDIAIITIAYAAMYYTFFKLFYDMRTQANSKFMLGFASASSSLFAF   219
K7_HMG1   174  LTDVFSENVTQADPFDVLINVTAYLMMFYTIFGLFNDMRKTG-SMFMLSASTVVNSASSL   232
AF273765   60  ---------------SDIIILTITRCIAILYIYFQFMRLRQLG-SKYILGIAGLFTIFSSF   104

ADK_HMGR  220  LLAVG-TAKIFNIRVSLLSLSEGIPFLVATVGFNRIVKLSAAVLNAAAVDKESHSIS---L   276
K7_HMG1   233  FLALYVTGCILGKEVSALTLFEGLPFIVVVVGFKHKIKIAGYALEKFERVGLSKRITTDE   292
AF273765  105  VFS---TVVIHFLDKELTGLNEALPFFLLLIDLSRASTLAKFALSSNSQDEVRENIA--R   159

ADK_HMGR  277  LIYRQLKDKALMFVKQLLCAAAFVGCSIYASHLEGLRSFCLLSAFIMIYDVLLTYSYYS   336
K7_HMG1   293  IVFESVSEEGGRLIQDKLLCIFAFIGCSMYAHQLKTLTMFGILSAFILIFELILTPTFYS   352
AF273765  160  ------GMAILGPTFTLDALVEQLVIGVGTMSG--VRQLEIMQCFGCMSVLANYFVFMFFP   213

ADK_HMGR  337  AVLALKVEINMIHQSIALKDALEEDGIPELAARQASLASFGSQKELSLGPNSGYVTAFKI   396
K7_HMG1   353  AILALREMNVIHRSTIIKDTLEEDGVVPSTARIISKAEKKSVS---SFLNLNVVVIIMKL   410
AF273765  214  ACVSLVLELSRESREGRPIMGLSHFARVLEEEENKPNPVTQRVK----MIMSLQLVLVHAH   270

ADK_HMGR  397  ASVAFFFAFHAYLVGSNMVFLSSMEDIIEG------HNLSKSIAKHISIGSTGTVVTLLEPK   452
K7_HMG1   411  SVILLFVFINFYNFGAMWVNDAFNSLYFDKER---VSLPDFITQNASENFKEQAIVSVTPL   468
AF273765  271  SRWIADPSPQNSTADTSKVSLGLDENVSKRIEPSVSLWQFYLSKMISMDIEQVTTLSLAL   330

ADK_HMGR  453  IYVPKNILFQ-VEDLVISILEKLSTAIRDKFISKTLFFLGTSSAINVYLLNAARAHSID   511
K7_HMG1   469  LYYKPIKSYQRIEDMILLLRMNVSVAIRDRFVSKLVLSALVCSAVINVYLLNAARIHTSY   528
AF273765  331  LLAVKYIFFEDTETESTLSLKNPITSP--VVTQKKVPDNCCRREPNLVRNNQKQDSVEEE   388
```

Figure 7-2

```
                  ▼ N-terminal (tHMGR)
ADK_HMGR  512  KPSQRLSKAIASKEASRRAKAAYE------------SQKSVSKSTDDTASSEPTFDV  556
K7_HMG1   529  TADQLVKTEVTKKSFTAPVQKASTPVLTNKTVISGSKVKSLSSAQSSSSGPSSSSEEDDS  588
AF273765  389  TGINRERKVEVIKPLVAETDTPNR------------ATFVVGNSSLLDTSSVLVTQ  432

ADK_HMGR  557  KNILPNSGIEHTFEELVDILKNGE--VSSLSNEEVTTLVVKDKLPLYALEKKLGDTTRAV  614
K7_HMG1   589  RDIESLDKKIRPLEEEALLSSGN--TKQLKNKEVAALVIHGKLPLYALEKKLGDTTRAV  646
AF273765  433  EPEIELPREPRPNEECLQILGNAEKGAKFLSDAEIIQLVNAKHIPAYKLETLMETHERGV  492

ADK_HMGR  615  AVRRQAISKLAKSPIVDSSSVPYLNYDYDKVFGACCENVIGYIPLPLGVAGPLLIDGKPF  674
K7_HMG1   647  AVRRKALSILAEAPVLASDRLPTYKNYDYDRVFGACCENVIGYMPLPVGVIGPLVIDGTSY  706
AF273765  493  SIRRQLLSKKLSEPSS-LQYLPYRDYNYSLVMGACCENVIGYMPIPVGVAGPLCLDEKEF  551

ADK_HMGR  675  HIPMATTEGCLVASTMRGCKAINAGGGVSTVLTRDGMTRGPCVKFPSLQRAGACKIWLDS  734
K7_HMG1   707  HIPMATTEGCLVASAMRGCKAINAGGGATIVLTKDGMTRGPVVRFPTLKRSGACKIWLDS  766
AF273765  552  QVPMATTEGCLVASTNRGCRAIGLGSGASSRVLADGMTRGPVVRLPRACDSAEVKAWLET  611
                     ▼ Sα2    ▼ NADP(H) binding site
ADK_HMGR  735  EEGQNLLKKSFNSTSRFARLQHVQTAIAGSLLFIRFRTTTGDAMGMNMISKGVEFTLKQM  794
K7_HMG1   767  EEGQNAIKKAFNSTSRFARLQHIQTCLAGDLLFMRFRTTTGDAMGMNMISKGVEYSLKQM  826
AF273765  612  SEGFAVIKEAFDSTSRFARLQKLHTSIAGRNLYIRFQSRSGDAMGMNMISKGTEKALSKL  671
                          ▼ HMG-CoA binding site
ADK_HMGR  795  VEEYGWSDMDVISVSGNYCTDKKAASINWIEGRGKSIVAEARIPGEVVRKVLKSDVDALV  854
K7_HMG1   827  VEEYGWEDMEVVSVSGNYCTDKKPAAINWIEGRGKSVVAEATIPGDVVRKVLKSDVSALV  886
AF273765  672  HEYF---PEMGILAVSGNYCTDKKPAAINWIEGRGKSVVCEAVIPAKVVREVLKTTTEAMI  729
                          ▲ Lα2
ADK_HMGR  855  ELNVSKNLIGSAMAGSIGGFNAHAANLVTAVFLACGQDPAQNVESSNCITLIDN----VDG  911
K7_HMG1   887  ELNIAKNLVGSAMAGSVGGFNAHAANLVTAVFLALGQDPAQNVESSNCITLMKE----VDG  943
AF273765  730  EVNINKNLVGSAMAGSTGGYNAHAANIVTAIYIACGQDAAQNVGSSNCITLMEASGPTNE  789

ADK_HMGR  912  DLGISVSMPSIEVGTIGGGTILEPQGAMLDLLGVRGPHPTTPGANAHQLAKVVASAVLAA  971
K7_HMG1   944  DLRISVSMPSIEVGTIGGGTVLEPQGAMLDLLGVRGPHATAPGTNARQLARIVACAVLAG  1003
AF273765  790  DLYISCTMPSIEIGTVGGGTNLLPQQACLQMLGVQGACKDNPGENARQLARIVCGTVMAG  849

ADK_HMGR  972  ELSLCSALAAGHLVQSHMQHNRGKPAAPAAAP-SSKADVQRLTDGSKICIKS  1022
K7_HMG1   1004 ELSLCAALAAGHLVQSHMTHNR-KPAEPTKPNNILDATDINRLKDGSVTCIKS  1054
AF273765  850  ELSLMAALAAGHLVKSHMIHNR-----------SKINLQDLQGACTKKTA-  888
```

MUTANT ENZYME AND PRODUCTION METHOD FOR TERPENOID USING SAID MUTANT ENZYME

CROSS-REFERENCE TO RELATED APPLICATIONS

This application is a national phase filing under 35 U.S.C. § 371 of PCT International Application No. PCT/JP2015/061168, filed on Apr. 9, 2015, which claims priority to Japanese Application No. 2014-080242, filed Apr. 9, 2014, the contents of which are hereby incorporated by reference in their entirety into the present application.

TECHNICAL FIELD

The present invention relates to a mutated enzyme and a method for preparing terpenoid using the same. According to the present invention, squalene, which is prepared through a mevalonate pathway, can be produced in large quantity.

BACKGROUND ART

Terpenoid means 50,000 or more natural compounds which has an isoprene unit with 5 carbon atoms as a basic skeleton. Terpenoid can be classified into hemiterpenes (C5), monoterpenes (C10), sesquiterpenes (C15), diterpenes (C20), sesquiterpenes (C25), triterpenes (C30), tetraterpenes (C40), and other polyterpenes, according to the number of carbon atoms thereof. In a biosynthesis thereof, various prenyl diphosphate having varying numbers of carbon atoms are prepared by condensation polymerization of isopentenylpyrophosphate (IPP) and dimethylallyl diphosphate (DMAPP) which is prepared by isomerization of isopentenyl diphosphate. Monoterpenes (C10) are biologically synthesized from geranyl diphosphate having 10 carbon atoms, sesterterpenes (C15) are biologically synthesized from farnesyl diphosphate having 15 carbon atoms, and diterpene and the like are biologically synthesized from geranylgeranyl diphosphate having 20 carbon atoms.

For a long time, it has been believed that IPP and DMAPP, which are necessary for the biosynthesis of terpenoid, are biologically synthesized only in the "mevalonate pathway" wherein the mevalonic acid is used. However, it becomes apparent that IPP and DMAPP are biologically synthesized through the methylerythritol phosphate (MEP) pathway, which is present in many eubacteria or plastid of plants (non-patent literature 1), in addition to the "mevalonate pathway".

As the terpenoid, in addition to unsaturated hydrocarbons of $(C5H8)n$, redox products thereof (alcohol, ketone, acid, etc.), compounds in which carbon(s) are removed, or the like, are found in bodies of many plants and animals, and many having a physiological activity are comprised therein. For example, the above terpenoids comprise compounds which have a key role in a living body, i.e., phytohormone such as abscisic acid, gibberellin, brassinosteroid, or juvenile hormone; or complex terpenes which have an isoprene structure as a part of the structure, such as chlorophyll, vitamin K, ubiquinone, and tRNA, which exhibit a useful physiological activity. Vitamin K is an important vitamin involved in a blood coagulation system, and is used as a hemostat. Recently, an involvement of vitamin K in bone metabolism is suggested, and thus it is expected that vitamin K is applied to a treatment of osteoporosis. Further, phylloquinone and menaquinone are approved as a medicine. Furthermore, ubiquinone and vitamin K(s) exhibit an inhibitory effect on adhesion of shellfish to a body of a ship or construction such as a bridge pier, and therefore it is expected that they are applied to paint for inhibiting adhesion of shellfish. Further, carotenoids exhibit antioxidant action, and thus it is expected that β-carotene, astaxanthin, cryptoxanthin, and the like, are effective in preventing cancer, or exhibits immunostimulatory activity.

CITATION LIST

Patent Literature

[Patent literature 1] Japanese Translation Publication (Kohyo) No. 2011-520471
[Patent literature 2] Japanese Translation Publication (Kohyo) No. 2009-538601
[Patent literature 3] Japanese Translation Publication (Kohyo) No. 2010-539902

Non-Patent Literature

[Non-patent literature 1] Bioscience, Biotechnology, and Biochemistry, (Japan) 2002, Vol. 66, p. 1691-1627
[Non-patent literature 2] "Kagaku to Seibutsu" (Japan) 2012, Vol. 50, p. 163-174
[Non-patent literature 3] Journal of Bacteriology (U.S.A) 1999, Vol. 181, p. 1256-1263
[Non-patent literature 4] The EMBO Journal (England) 2000, Vol. 19, p. 819-830
[Non-patent literature 5] Applied Microbiology and Biotechnology (1998) 49: p. 66-71

SUMMARY OF INVENTION

Technical Problem

As pathways involved in terpenoid synthesis are revealed, an improvement of terpenoid productivity is examined by improving the pathways (Non-patent literature 2). One terpenoid therein, i.e., squalene is biologically synthesized directly from farnesyl diphosphate, and is considered as a main intermediate for various triterpenes in the pathway. Therefore, various approaches for improving the amount of squalene production are conducted. For example, Patent literature 1 discloses a compound comprising genetically mutated yeast which is modified so as to produce an increased concentrated isoprenoid, and states that the amount of squalene production is increased by deleting a membrane-bound domain of the hydroxymethylglutaryl CoA reductase (HMGR). Further, Patent literature 2 and Patent literature 3 disclose a method for producing isoprenoids compound including squalene.

However, the amount of squalene production described in Patent literature 1 is at most about 5% by weight with respect to a dry fungal weight, and thus it is inadequate. Further, Patent literature 2 and Patent literature 3 disclose the techniques for adjusting conditions of manufacture, but the techniques cannot greatly exceed the conventional art.

The object of the present invention is to efficiently produce useful terpenoid compounds, and specifically, to provide a method for preparing squalene, which is an important intermediate of terpenoid.

Solution to Problem

The inventors have conducted intensive studies into a method for preparing a terpenoid compound. As a consequence, the inventors have found that an amount of the compounds produced in a downstream of the mevalonate pathway, in particular, an amount of squalene is dramatically increased by using a hydroxymethylglutaryl CoA reductase having specific amino acid sequences as the hydroxymethylglutaryl CoA reductase, which is one of the enzymes in the mevalonate pathway.

The present invention is based on the above findings.

[1] a hydroxymethylglutaryl CoA reductase (HMGR) comprising: (a) an amino acid other than alanine (A) at the 10th position in an Sα2 amino acid sequence of HMGR, (b) an amino acid other than proline (P) at the 1st position from the carboxyl terminal in the DKK region of the HMG-CoA binding site of HMGR, (c) an amino acid other than alanine (A) at the 1st position in an Lα2 amino acid sequence of HMGR, and (d) an amino acid other than glutamic acid (E) at the 6th position in an Lα2 amino acid sequence of HMGR,

[2] the hydroxymethylglutaryl CoA reductase of the item [1], wherein the 10th amino acid in an Sα2 amino acid sequence is serine (S), the 1st amino acid from the carboxyl terminal in the DKK region of the HMG-CoA binding site is alanine (A), the 1st amino acid in an Lα2 amino acid sequence is serine (S), and the 6th amino acid in an Lα2 amino acid sequence is asparagine (N),

[3] the hydroxymethylglutaryl CoA reductase of the item [1] or [2], further comprising one or more amino acids selected from the group consisting of: (e) an amino acid other than isoleucine (I) at the 7th position in an Sα2 amino acid sequence of HMGR, (f) an amino acid other than isoleucine (I) at the 5th position in an Lα2 amino acid sequence of HMGR, and (g) an amino acid other than alanine (A) at the 6th position in an Sα2 amino acid sequence of HMGR,

[4] the hydroxymethylglutaryl CoA reductase of the item [3], wherein the 7th amino acid in an Sα2 amino acid sequence is leucine, the 5th amino acid in an Lα2 amino acid sequence is threonine, the 6th amino acid in an Sα2 amino acid sequence is leucine,

[5] the hydroxymethylglutaryl CoA reductase of the items [1] to [4], wherein the hydroxymethylglutaryl CoA reductase is a polypeptide comprising any one of (1) the 514th to 1022nd amino acids in the amino acid sequence of SEQ ID NO: 1, (2) amino acids wherein one or multiple amino acids are deleted, substituted, inserted, and/or added in the 514th to 1022nd amino acids in the amino acid sequence of SEQ ID NO: 1, or (3) amino acids having the homology of 80% or higher with the 514th to 1022nd amino acids in the amino acid sequence of SEQ ID NO: 1; and exhibiting hydroxymethylglutaryl CoA reductase activity,

[6] the hydroxymethylglutaryl CoA reductase of the items [1] to [5], wherein the hydroxymethylglutaryl CoA reductase is a polypeptide consisting of any one of the: (1) amino acids of SEQ ID NO: 1, (2) amino acids wherein one or plural amino acids are deleted, substituted, inserted, and/or added in the amino acid sequence of SEQ ID NO: 1, or (3) amino acids having the homology of 80% or higher with the amino acid sequence of SEQ ID NO: 1; and exhibiting hydroxymethylglutaryl CoA reductase activity,

[7] the hydroxymethylglutaryl CoA reductase of the items [1] to [6], which does not comprise membrane-bound domain,

[8] a polynucleotide encoding the hydroxymethylglutaryl CoA reductase of the items [1] to [7],

[9] a microorganism having the polynucleotide of the item [8],

[10] a vector having the polynucleotide of the item [8],

[11] a transformant having the vector of the item [10]

[12] a method for preparing terpenoid characterized in that the transformant of the item [11] is cultured.

The hydroxymethylglutaryl CoA reductase of the item [1] may be [13] the hydroxymethylglutaryl CoA reductase of the item [1], wherein an amino acid at the 10th position in an Sα2 amino acid sequence of hydroxymethylglutaryl CoA reductase (HMGR) is an amino acid other than alanine (A), an amino acid at the 2nd position in the amino acid sequence from the amino terminus of an Lα2 amino acid sequence to the amino terminus of HMGR is an amino acid other than proline (P), an amino acid at the 1st position in an Lα2 amino acid sequence is an amino acid other than alanine (A), an amino acid at the 5th position in an Lα2 amino acid sequence is an amino acid other than isoleucine (I), and an amino acid at the 6th position in an Lα2 amino acid sequence is an amino acid other than glutamic acid (E), and an activity thereof is increased compared to a hydroxymethylglutaryl CoA reductase wherein an amino acid at the 10th position in an Sα2 amino acid sequence is alanine (A), an amino acid at the 2nd position in the amino acid sequence from the amino terminus of an Lα2 amino acid sequence to the amino terminus of HMGR is proline (P), an amino acid at the 1st position in an Lα2 amino acid sequence is alanine (A), an amino acid at the 5th position in an Lα2 amino acid sequence is isoleucine (I), an amino acid at the 6th position in an Lα2 amino acid sequence is glutamic acid (E), and amino acids other than those listed above are identical with the hydroxymethylglutaryl CoA reductase; or

[14] the hydroxymethylglutaryl CoA reductase of the item [1], wherein an amino acid at the 10th position in an Sα2 amino acid sequence is serine (S), an amino acid at the 2nd position in the amino acid sequence from the amino terminus of an Lα2 amino acid sequence to the amino terminus of HMGR is alanine (A), an amino acid at the 1st position in an Lα2 amino acid sequence is serine (S), an amino acid at the 5th position in an Lα2 amino acid sequence is threonine (T), and an amino acid at the 6th position in an Lα2 amino acid sequence is asparagine (N).

Advantageous Effects of Invention

According to the mutated enzyme and method for preparing terpenoid using the mutated enzyme, useful terpenoid compounds can be effectively produced. For example, an amount of mevalonic acid production in the mevalonate pathway can be increased by using the hydroxymethylglutaryl CoA reductase of the present invention. Further, squalene which is an important intermediate of terpenoid can be effectively produced in large quantity.

In addition, the following legend symbols are accession numbers of UniProt (Universal Protein Resource<www.uniprot.org/>): Q6BSE8: amino acid sequence of *Debaryomyces hansenii* (ATCC 36239)/G3AY61: amino acid sequence of *Candida tenuis* (ATCC 10573)/J8PYR1: amino acid sequence of *Saccharomyces arboricola* (strain H-6)/G8B666: amino acid sequence of *Candida parapsilosis* (ATCC MYA-4646)/A3LX63: amino acid sequence of *Scheffersomyces stipites* (ATCC 58785)/H2AW26: amino acid sequence of *Kazachstania africana* (ATCC 22294)/G8Y9W2: *Pichia sorbitophila* (ATCC MYA-4447)/F2QRB0: amino acid sequence of *Komagataella pastoris* (ATCC 76273).

FIG. 3 shows aligned amino acid sequences of DKK region of HMG-CoA binding site and around Lα2 of ADK4653_HMGR of the present invention and HMGRs which are currently reported. The legend symbols are same as those of FIG. 2.

FIG. 4 is a graph showing an increased production of mevalonic acid using a sake yeast (*Saccharomyces cerevisiae* strain K701) comprising a full length ADK4653 gene.

Figure 5:
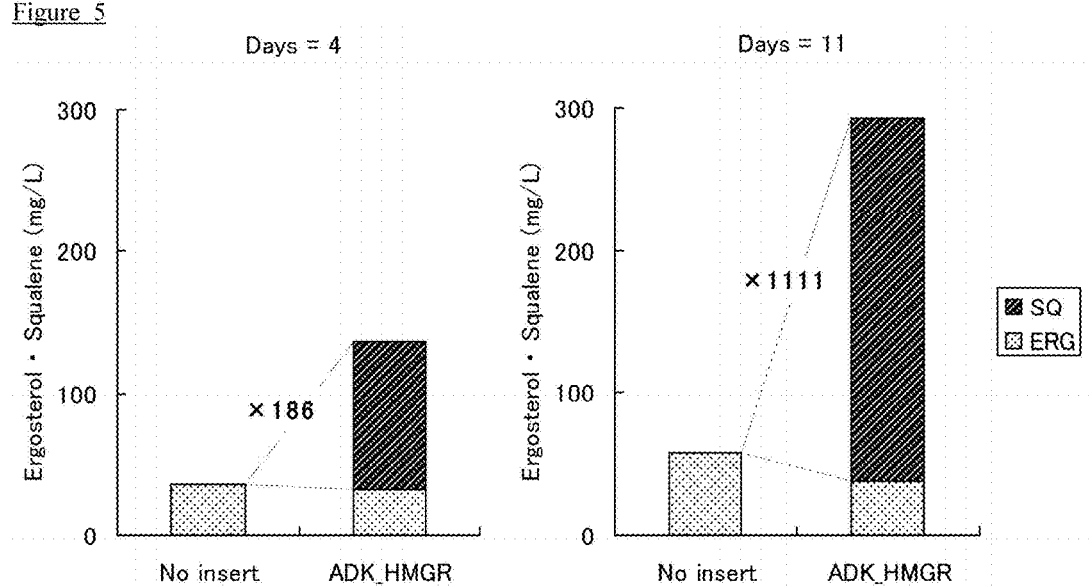

FIG. 5 is a graph showing a squalene production using a sake yeast comprising a full length ADK4653 gene. (SQ: squalene, ERG: ergosterol)

Figure 6:
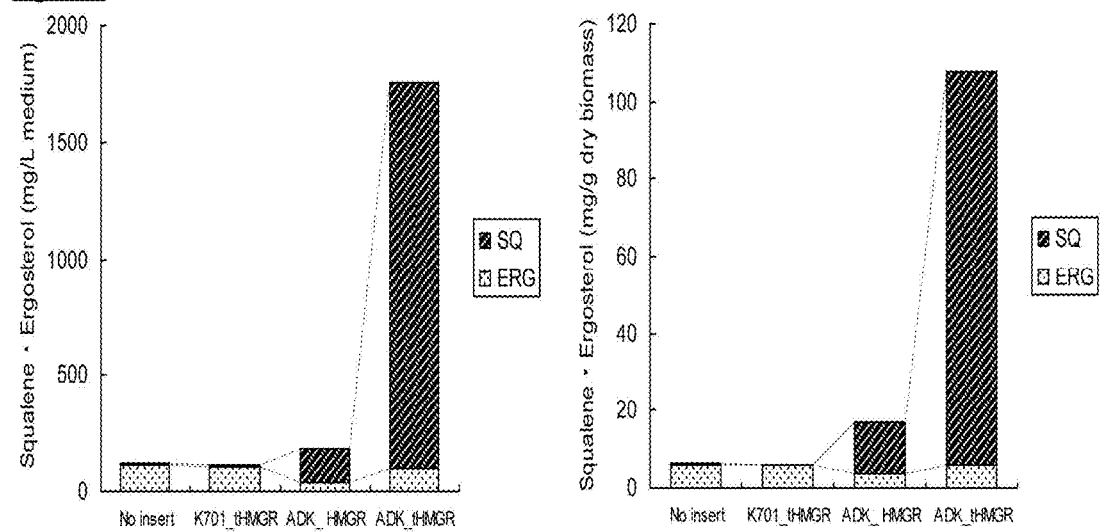

FIG. 6 is a graph showing squalene productions using a sake yeast comprising a truncated ADK4653 gene or a truncated sake yeast HMGR gene. (SQ: squalene, ERG: ergosterol)

Figures 1, 2:
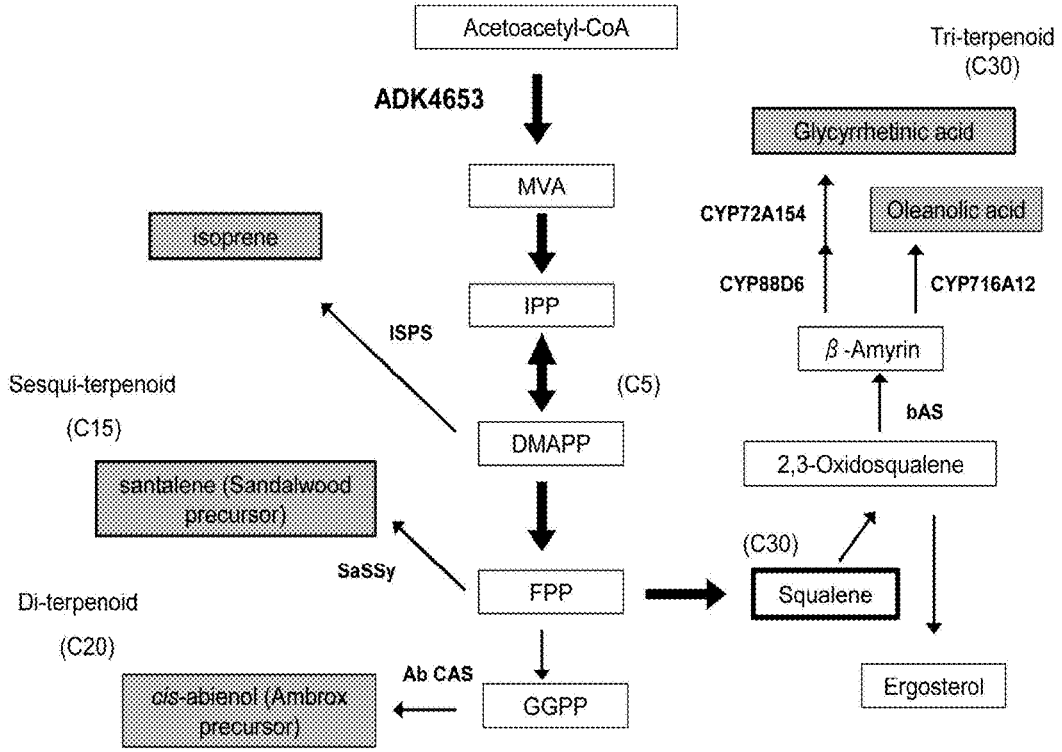
FIG. 1 is a schematic view showing a mevalonate pathway and a production pathway of terpenoid compounds which lies downstream thereof.
FIG. 2 shows aligned amino acid sequences of around Sα2 of ADK4653 HMGR of the present invention and HMGRs which are currently reported. The legend symbols are as follows: ADK_HMGR: amino acid sequence of the present invention/HMG1: amino acid sequence of *Saccharomyces cerevisiae* (DDBJ accession No. is M22002)/HMG2: amino acid sequence of *Saccharomyces cerevisiae* (DDBJ accession No. is M22255)/AF273765: amino acid sequence of enzyme derived from *Homo sapiens* (Human) (DDBJ: DNA Data Bank of Japan<www.ddbj.nig.ac.jp/>).

FIG. 7-1 is a view showing a comparison of amino acid sequences of ADK4653HMGR, sake yeast HMGR, and an enzyme protein derived from a human. The legend symbols are as follows: ADK_HMGR: amino acid sequence of the enzyme of the present invention/K7 HMG1: amino acid sequence of enzyme derived from *Saccharomyces cerevisiae* strain K 7 (DDBJ accession No. DG000049, CDS 114719.117883)/AF273765: amino acid sequence of enzyme protein derived from *Homo sapiens* (human) (DDBJ accession No. AF273765)

FIG. 7-2 is a view sowing a comparison of amino acid sequences of ADK4653HMGR, sake yeast HMGR, an enzyme protein derived from a human. The legend symbols are the same as those of FIG. 7-1.

Figure 8:
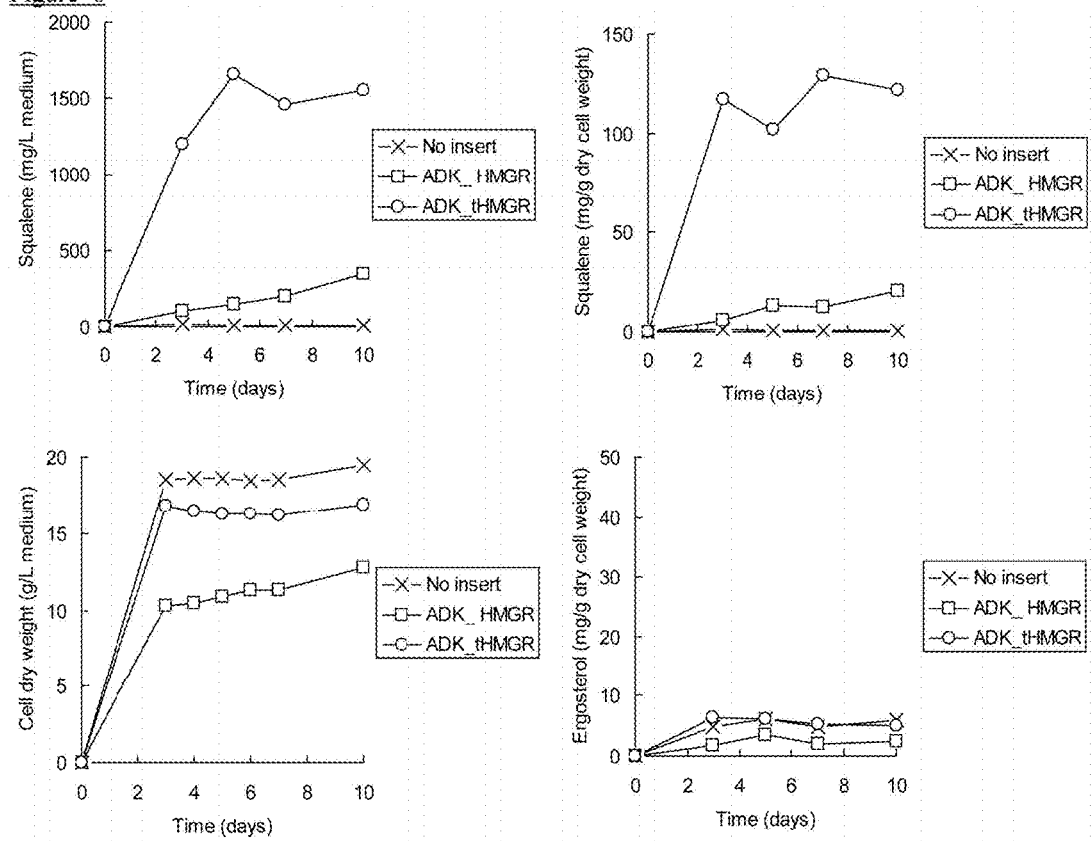

FIG. 8 is a graph showing time courses of squalene production using a sake yeast comprising a full length ADK4653 gene or a truncated ADK4653 gene.

Figure 9:
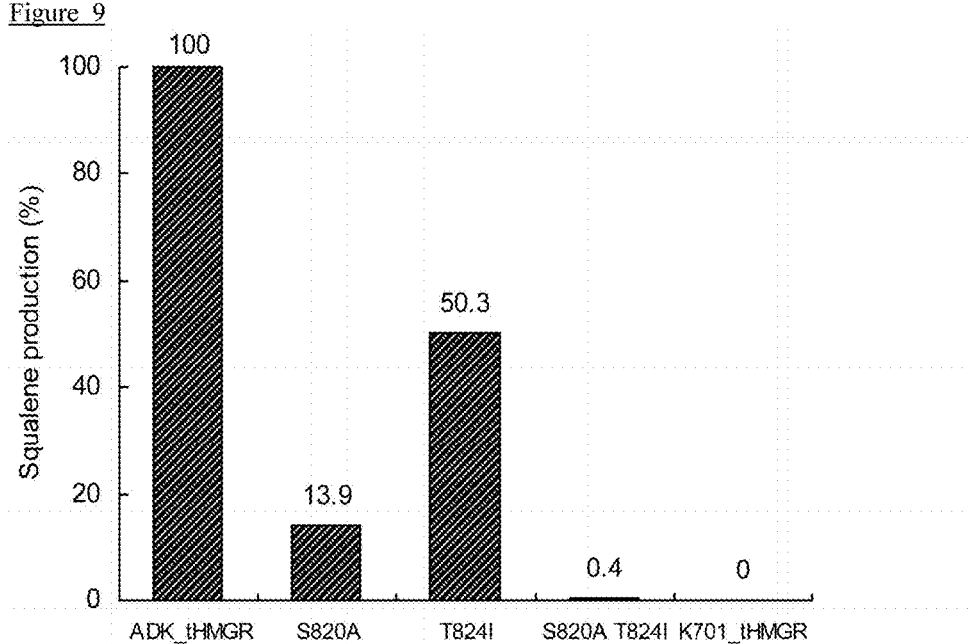

FIG. 9 is a graph showing that amounts of squalene production using yeast having (c) a mutation from serine to alanine at the 1st position in an Lα2 amino acid sequence of ADK4653HMGR, (f) a mutation from threonine to isoleucine at the 5th position in an Lα2 amino acid sequence of ADK4653HMGR, or a combination thereof, are examined.

Figure 10:
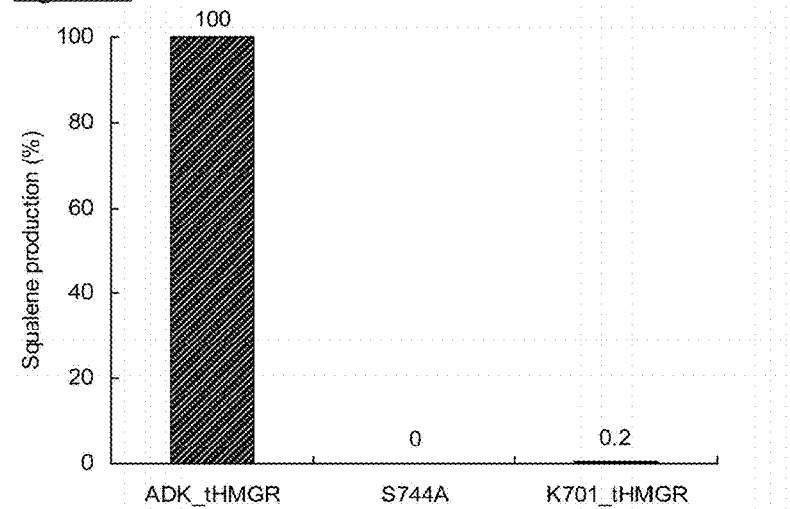

FIG. 10 is a graph showing that an amount of squalene production using yeast having (a) a mutation from serine to alanine at the 10th position in an Sα2 amino acid sequence of ADK4653HMGR is examined.

Figure 11:
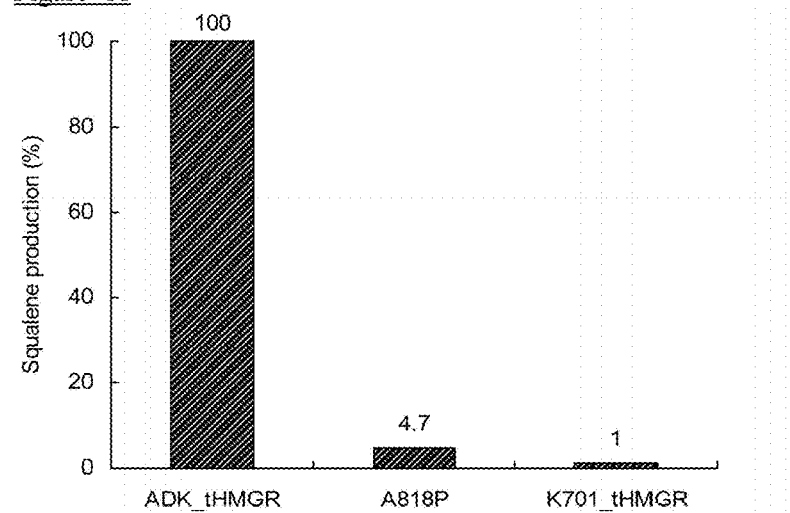

FIG. 11 is a graph showing that an amount of squalene production using yeast having (b) a mutation from alanine to proline at the 1st position from the C terminus of the DKK region of the HMG-CoA binding site (2nd position from the amino terminus of an Lα2 amino acid sequence to the amino terminus of HMGR) is examined.

Figure 12:
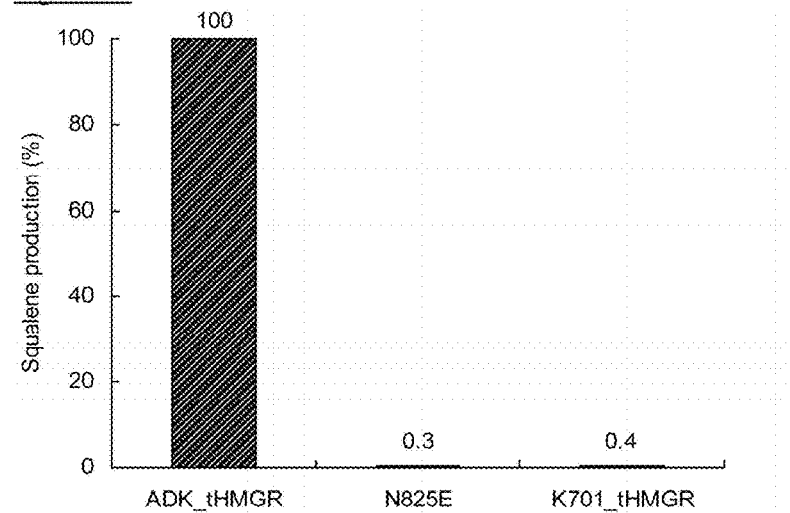

FIG. 12 is a graph showing that an amount of squalene production using yeast having (d) a mutation from asparagine to glutamic acid at the 6th position in an Lα2 amino acid sequence of ADK4653HMGR is examined.

Figure 13:
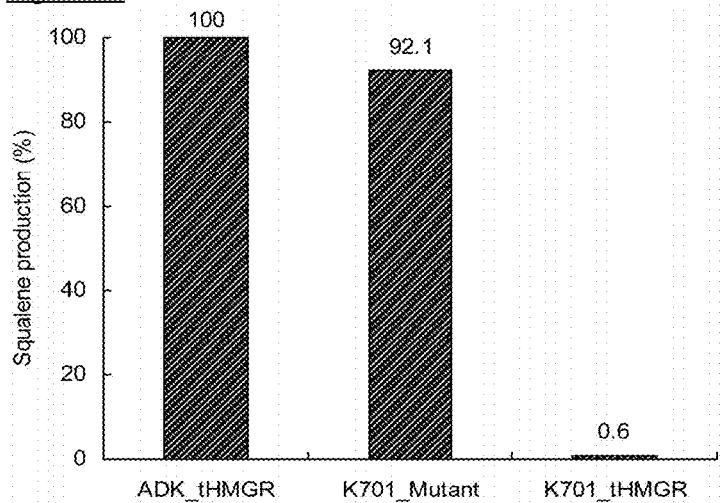

FIG. 13 is a graph showing that an amount of squalene production using a yeast expressing mutated enzyme (K701_Mutant) wherein three mutations in amino acids constituting Sα2, one mutation positioned between HMG-CoA binding site and Lα2, and three mutations in amino acids constituting Lα2 in the amino acid sequence of truncated HMGR of sake yeast (K701 strain) are introduced, is examined. Specifically, an amount of squalene production using a yeast having (e) a mutation from isoleucine to leucine at the 7th position in an Sα2 region, (a) a mutation from alanine to serine at the 10th position in an Sα2 region, (g) a mutation from alanine to leucine at the 6th position in an Sα2 region, (b) a mutation from proline to alanine at the 1st position from the C terminus of the DKK region of the HMG-CoA binding site (2nd position from the amino terminus of an Lα2 region to the amino terminus of HMGR), (c) a mutation from alanine to serine at the 1st position in an Lα2 region, (f) a mutation from isoleucine to threonine at the 5th position in an Lα2 region, and (d) a mutation from glutamic acid to asparagine at the 6th position in an Lα2 region, in the amino acid sequence of a truncated HMGR of sake yeast (K701 strain), is examined.

Figure 14:
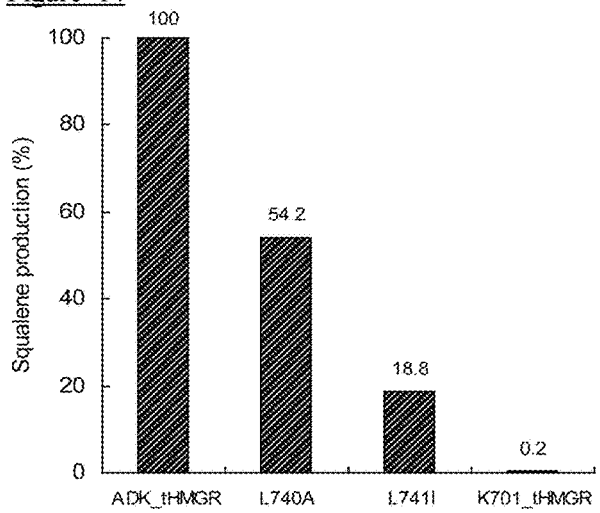

FIG. 14 is a graph showing the amounts of squalene production using yeasts having (g) a mutation from leucine to alanine at the 6th position in an Sα2 amino acid sequence of ADK4653HMGR (Example 7), or (e) a mutation from leucine to isoleucine at the 7th position in an Sα2 amino acid sequence of ADK4653HMGR (Example 7) are examined.

Figure 15:
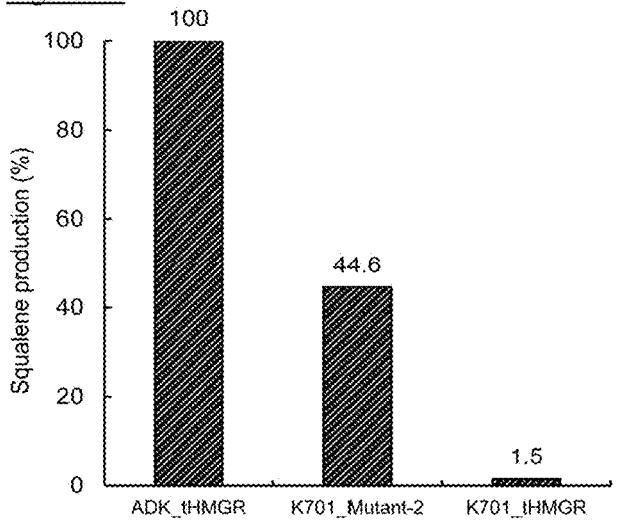

FIG. 15 is a graph showing that an amount of squalene production using a yeast having (e) a mutation from isoleucine to leucine at the 7th position in an Sα2 region, (a) a mutation from alanine to serine at the 10th position in an Sα2 region, (b) a mutation from proline to alanine at the 1st position from the C terminus of the DKK region of the HMG-CoA binding site (2nd position from the amino terminus of an Lα2 region to the amino terminus of HMGR), (c) a mutation from alanine to serine at the 1st position in an Lα2 region, (f) a mutation from isoleucine to threonine at the 5th position in an Lα2 region, (d) a mutation from glutamic acid to asparagine at the 6th position in an Lα2 region, in an amino acid sequence of truncated HMGR of sake yeast (K701 strain) is examined (Example 9).

Figure 16:
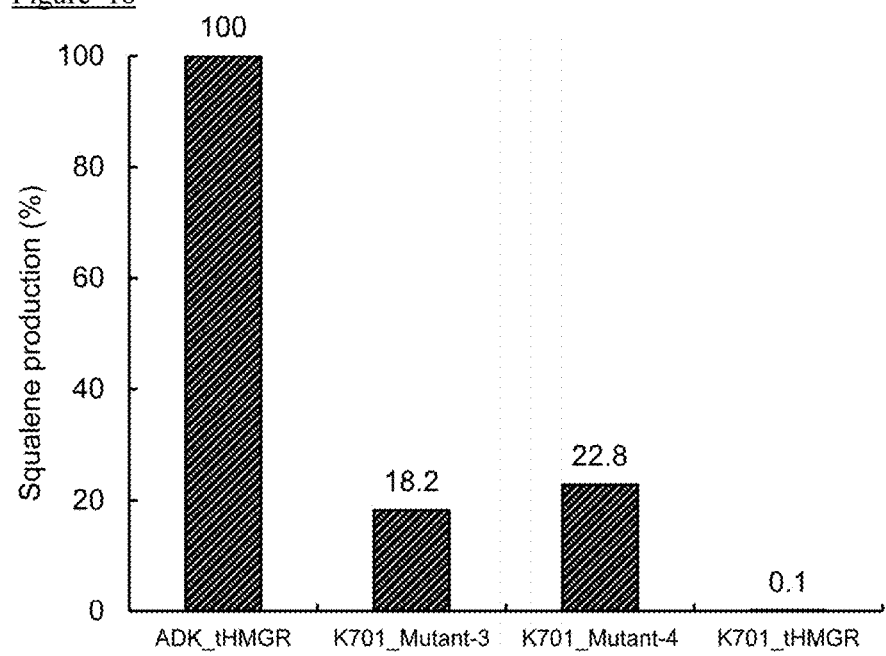

FIG. 16 is a graph showing that an amount of squalene production using a yeast having (e) a mutation from isoleucine to leucine at the 7th position in an Sα2 region, (a) a mutation from alanine to serine at the 10th position in an Sα2 region, (b) a mutation from proline to alanine at the 1st position from the C terminus of the DKK region of the HMG-CoA binding site (2nd position from the amino terminus of an Lα2 region to the amino terminus of HMGR), (c) a mutation from alanine to serine at the 1st position in an Lα2 region, (d) a mutation from glutamic acid to asparagine at the 6th position in an Lα2 region, in an amino acid sequence of a truncated HMGR of sake yeast (K701 strain) is examined (Example 10); and an amount of squalene production using a yeast having (e) a mutation from isoleucine to leucine at the 7th position in an Sα2 region, (a) a mutation from alanine to serine at the 10th position in an Sα2 region, (g) a mutation from alanine to leucine at the 6th position in an Sα2 region, (b) a mutation from proline to alanine at the 1st position from the C terminus of the DKK region of the HMG-CoA binding site (2nd position from the amino terminus of an Lα2 region to the amino terminus of HMGR), (c) a mutation from alanine to serine at the 1st position in an Lα2 region, (d) a mutation from glutamic acid to asparagine at the 6th position in an Lα2 region, in an amino acid sequence of a truncated HMGR of sake yeast (K701 strain) is examined (Example 11).

DESCRIPTION OF EMBODIMENTS

[1] Hydroxymethylglutaryl CoA Reductase

The hydroxymethylglutaryl CoA reductase of the present invention comprises (a) an amino acid other than alanine (A) at the 10th position in an S$\alpha$2 amino acid sequence of HMGR, (b) an amino acid other than proline (P) at the 1st position from the carboxy terminus in the DKK region of the HMG-CoA binding site of HMGR, (c) an amino acid other than alanine (A) at the 1st position in an L$\alpha$2 amino acid sequence of HMGR, and (d) an amino acid other than glutamic acid (E) at the 6th position in an L$\alpha$2 amino acid sequence of HMGR. Further, the 10th amino acid in an S$\alpha$2 amino acid sequence is preferably serine (S), the 1st amino acid from carboxy terminus in DKK region of HMG-CoA binding site is preferably alanine (A), the 1st amino acid in an L$\alpha$2 amino acid sequence is preferably serine (S), and the 6th amino acid in an L$\alpha$2 amino acid sequence is preferably asparagine (N).

Further, the hydroxymethylglutaryl CoA reductase may comprise one or more amino acids selected from the group consisting of: (e) an amino acid other than isoleucine (I) at the 7th position in an S$\alpha$2 amino acid sequence of HMGR, (f) an amino acid other than isoleucine (I) at the 5th position in an L$\alpha$2 amino acid sequence of HMGR, and (g) an amino acid other than alanine (A) at the 6th position in an S$\alpha$2 amino acid sequence of HMGR. The 7th amino acid in an S$\alpha$2 amino acid sequence is preferably leucine, the 5th amino acid in an L$\alpha$2 amino acid sequence is preferably threonine, the 6th amino acid in an S$\alpha$2 amino acid sequence is preferably leucine.

An activity of the hydroxymethylglutaryl CoA reductase of the present invention is increased compared to a hydroxymethylglutaryl CoA reductase wherein (a) an amino acid at the 10th position in an S$\alpha$2 amino acid sequence is alanine (A), (b) an amino acid at the 1st position from the carboxy terminus in the DKK region of the HMG-CoA binding site of HMGR is proline, (c) an amino acid at the 1st position in an L$\alpha$2 amino acid sequence is alanine (A), (d) an amino acid at the 6th position in an L$\alpha$2 amino acid sequence is glutamic acid (E), (e) an amino acid at the 7th position in an S$\alpha$2 amino acid sequence is isoleucine (I), (f) an amino acid at the 5th position in an L$\alpha$2 amino acid sequence is isoleucine (I), (g) an amino acid at the 6th position in an S$\alpha$2 amino acid sequence is alanine (A).

In connection to this, "(b) the amino acid at the 1st position from carboxy terminus in the DKK region of the HMG-CoA binding site of HMGR" is located in the position identical with "an amino acid existed at the 2nd position from amino terminus of an L$\alpha$2 region to amino terminus of HMGR"

<<Hydroxymethylglutaryl CoA Reductase>>

Hydroxymethylglutaryl CoA reductase (hereinafter sometimes referred to as an HMGR) is a membrane-associated protein which is composed of a membrane-binding site and an active site. HMGR reduces 3-hydroxy-3-methylglutaryl CoA (hereinafter sometimes referred to as an HMGCoA) and converts it into mevalonic acid (MVA) in the mevalonate pathway. In the active site, regions which are referred to as motifs A to G are highly conserved in eukaryotic, eubacteria, and ancient bacteria (Non-patent literature 3). Further, L$\alpha$1 to 9 regions, L$\beta$1 to 6 regions, S$\alpha$1 to 3 regions, and S$\beta$1 to 4 regions are identified by a crystal analysis of human HMGR (Non-patent literature 4).

The HMGR used in the present invention is preferably eukaryotic or ancient bacteria derived HMGR, more preferably eukaryotic-derived HMGR. As mentioned above, the active sites of HMGR are highly conserved, and in particular, greater effects of eukaryotic or ancient bacteria-derived HMGR can be expected.

One of the distinctive amino acids in the hydroxymethylglutaryl CoA reductase of the present invention is (a) an amino acid other than alanine (A) which is present at the 10th position in an S$\alpha$2 region, as shown in FIG. 2. The amino acid is not limited, but an amino acid which destroys a helix structure, such as serine, tyrosine, glycine, or proline, or an amino acid which has no effect on a helix structure, such as isoleucine, valine, cysteine, threonine, or asparagine is preferable. The most preferable amino acid is serine(S). Further, one of the distinctive amino acids in the hydroxymethylglutaryl CoA reductase of the present invention is (b) an amino acid other than proline (P) which is present at the 1st position from the carboxy terminus in the DKK region of the HMG-CoA binding site of HMGR (at the 2nd position from amino terminus of an L$\alpha$2 region to amino terminus of HMGR), as shown in FIG. 3. The amino acid other than proline (P) is not limited, but an amino acid which strongly forms a helix structure, such as glutamic acid, alanine, methionine, leucine, lysine, histidine, glutamine, phenylalanine, aspartic acid, or an amino acid which has a tendency to form a helix structure, such as tryptophan, arginine. The most preferable amino acid is alanine.

Further, one of the distinctive amino acids in the hydroxymethylglutaryl CoA reductase of the present invention is (c) an amino acid other than alanine (A) present at the 1st position in an L$\alpha$2 region of HMGR, as shown in FIG. 3.

The amino acid is not limited, but an amino acid which destroys a helix structure, such as serine, tyrosine, glycine, or proline, or an amino acid which has no effect on a helix structure, such as isoleucine, valine, cysteine, threonine, or asparagine is preferable. The most preferable amino acid is serine(S).

One of the distinctive amino acids in the hydroxymethylglutaryl CoA reductase of the present invention is (d) an amino acid other than glutamic acid (E) present at the 6th position in an L$\alpha$2 region of HMGR, as shown in FIG. 3. The amino acid other than glutamic acid (E) is not limited, but an amino acid which destroys a helix structure, such as serine, tyrosine, glycine, or proline, or an amino acid which has no effect on a helix structure, such as isoleucine, valine, cysteine, threonine, or asparagine is preferable. The most preferable amino acid is asparagine (N).

One of the preferable amino acids in the hydroxymethylglutaryl CoA reductase of the present invention is (e) an amino acid other than isoleucine (I) present at the 7th position in an S$\alpha$2 region of HMGR. The amino acid other than isoleucine (I) is not particularly limited, but can include serine, tyrosine, glycine, proline, isoleucine, valine, cysteine, threonine, asparagine, or leucine. In particular, an amino acid which has a tendency to form a helix structure, and the most preferable amino acid, is leucine (L).

One of the preferable amino acids in the hydroxymethylglutaryl CoA reductase of the present invention is (e) an amino acid other than isoleucine (I) present at the 5th position in an L$\alpha$2 region of HMGR, as shown in FIG. 3. The amino acid is not limited, but an amino acid which destroys a helix structure, such as serine, tyrosine, glycine, or proline, or an amino acid which has no effect on a helix structure, such as valine, cysteine, threonine, or asparagine is preferable. The most preferable amino acid is threonine (T).

One of the preferable amino acids in the hydroxymethylglutaryl CoA reductase of the present invention is (g) an amino acid other than alanine (A) present at the 6th position in an Sα2 amino acid sequence of HMGR. The amino acid other than alanine (A) is not particularly limited, but is preferably serine, tyrosine, glycine, proline, isoleucine, valine, cysteine, threonine, asparagine, or leucine, and most preferably leucine (L).

As shown in Table 1, it is important that, in particular, the four amino acids positioned in (a), (b), (c), and (d) among the seven amino acids positioned in (a), (b), (c), (d), (e), (f), and (g) are respectively an amino acid other than alanine (A), an amino acid other than proline (P), an amino acid other than alanine (A), and an amino acid other than glutamic acid (E). Specifically, as is clear from the results of Comparative Examples 3 to 6, if any one of the amino acids positioned in (a), (b), (c), and (d) of ADK4653_tHMGR is replaced with the amino acids positioned in (a), (b), (c), and (d) of K701_tHMGR, the relative values of the amount of squalene production are dramatically decreased to 0 to 13.9. Therefore, the amino acids positioned in (a), (b), (c), and (d) are particularly important in the squalene production.

Further, as is clear from the results of Examples 6 to 11, when any one of the amino acids positioned in (e), (f), and (g) is an amino acid other than isoleucine (I), an amino acid other than isoleucine (I), or an amino acid other than alanine (A), respectively, the resulting sake yeasts exhibit an excellent squalene production amount compared to K701_tHMGR.

As is clear from the results of Comparative Example 2 and Example 3, ADK4653_tHMGR (a=S, b=A, c=S, d=N, e=L, f=T, g=L) wherein the amino acids positioned in (a), (b), (c), (d), (e), (f), and (g) are different from the amino acids of K701_tHMGR (a=A, b=P, c=A, d=E, e=I, f=I, g=A), exhibits an exceptional ability to produce squalene. Further, as is clear from the results of Example 5, the relative value of the amount of squalene production reaches 92.1, i.e., about the same level of ADK4653_tHMGR, by substituting the seven amino acids positioned in (a), (b), (c), (d), (e), (f), and (g) of K701_tHMGR with the seven amino acids of ADK4653_tHMGR. Lengths of amino acid sequences of ADK4653_tHMGR and K701_tHMGR differ from one another, and the identity of truncated HMGRs (tHMGRs) of ADK4653_tHMGR and K701_tHMGR is 78%. Therefore, it is surprising that the amount of squalene production reaches the same level of ADK4653_tHMGR by substituting a mere 7 amino acids in the amino acids of K701_tHMGR with the amino acids of ADK4653_tHMGR.

The length of the Sα2 region is 12 amino acids. The amino acid sequences of the currently-reported Sα2 are (E/I/S), E, G, (Q/S/F), (N/K/S/A), (L/A/S/TN), (I/V/M), K, (K/N/E), A, F, (N/D) in order. To the best of the inventor's knowledge, the currently-reported amino acid as the 10th amino acid in an Sα2 region is only alanine (A), and thus a hydroxymethylglutaryl CoA reductase having an amino acid other than alanine has not been reported.

Further, the length of the Lα2 region is 6 amino acids. The amino acid sequences of the currently-reported Lα2 are A, I, N, W, (I/L), (E/N) in order. The currently-reported amino acid as the 1st amino acid in an Lα2 region is only alanine (A), and thus a hydroxymethylglutaryl CoA reductase having an amino acid other than alanine has not been reported. In addition, the currently-reported amino acids as the 5th amino acid in an Lα2 region are only leucine (L) and isoleucine (I), and thus a hydroxymethylglutaryl CoA reductase having an amino acid other than leucine and isoleucine has not been reported. Furthermore, the currently-reported amino acid as the 6th amino acid in an Lα2 region is almost glutamic acid (E), and only one hydroxymethylglutaryl CoA reductase having asparagine (N) has been reported, to the best of the inventor's knowledge. Further, the currently-reported amino acid at the 2nd position from amino terminus of an Lα2 region to amino terminus of HMGR is almost proline (P), and only three types of hydroxymethylglutaryl CoA reductase having valine (V), alanine (A), or serine (S) are reported.

The HMG-CoA binding site plays an important role in a HMGR activity. A part of the HMG-CoA binding site located in an area which exists at several amino acids from the Lα2 region to amino terminus, and a sequence of aspartic acid (D), lysine (K), and lysine (K) is highly conserved therein (Non-patent literature 4).

In the hydroxymethylglutaryl CoA reductase of the present invention, it is most preferable that the seven amino acids of (a) to (g) are (a) an amino acid other than alanine (A), (b) an amino acid other than proline (P), (c) an amino acid other than alanine (A), (d) an amino acid other than glutamic acid (E), (e) an amino acid other than isoleucine (I), (f) an amino acid other than isoleucine (I), and (g) an amino acid other than alanine (A), respectively.

However, the hydroxymethylglutaryl CoA reductase wherein the four amino acids of (a) to (d) are (a) an amino acid other than alanine (A), (b) an amino acid other than proline (P), (c) an amino acid other than alanine (A), and (d) an amino acid other than glutamic acid (E), respectively, is also preferable. Further, the hydroxymethylglutaryl CoA reductase wherein any one of amino acids of (e) to (g) in addition to the above four amino acids of (a) to (d) is (e) an amino acid other than isoleucine (I), (f) an amino acid other than isoleucine (I), or (g) an amino acid other than alanine (A), respectively, is also preferable (i.e., 5 amino acids are substituted.). Furthermore, the hydroxymethylglutaryl CoA reductase wherein two of the amino acids of (e) to (g) in addition to the above four amino acids of (a) to (d) are (e) an amino acid other than isoleucine (I), (f) an amino acid other than isoleucine (I), or (g) an amino acid other than alanine (A), respectively, is also preferable (i.e., 6 amino acids are substituted.).

Further, the hydroxymethylglutaryl CoA reductase wherein 6 or more amino acids selected from the amino acids (a) to (g) are (a) an amino acid other than alanine (A), (b) an amino acid other than proline (P), (c) an amino acid other than alanine (A), (d) an amino acid other than glutamic acid (E), (e) an amino acid other than isoleucine (I), (f) an amino acid other than isoleucine (I), and (g) an amino acid other than alanine (A), respectively, is also preferable. For example, 6 amino acids of (a), (b), (c), (d), (f), and (g) may be (a) an amino acid other than alanine (A), (b) an amino acid other than proline (P), (c) an amino acid other than alanine (A), (d) an amino acid other than glutamic acid (E), (f) an amino acid other than isoleucine (I), and (g) an amino acid other than alanine (A), respectively, and 6 amino acids of (a) to (f) may be (a) an amino acid other than alanine (A), (b) an amino acid other than proline (P), (c) an amino acid other than alanine (A), (d) an amino acid other than glutamic acid (E), (e) an amino acid other than isoleucine (I), and (f) an amino acid other than isoleucine (I), respectively.

An activity of the hydroxymethylglutaryl CoA reductase of the present invention is increased compared to a hydroxymethylglutaryl CoA reductase wherein an amino acid at the 10th position in an Sα2 amino acid sequence is alanine (A), an amino acid at the 1st position from carboxy terminus in the DKK region of the HMG-CoA binding site is proline (P), an amino acid at the 1st position in an Lα2 amino acid sequence is alanine (A), an amino acid at the 6th position in an Lα2 amino acid sequence is glutamic acid (E), and amino acids other than those listed above are identical with the hydroxymethylglutaryl CoA reductase. That is to say, the activity of the hydroxymethylglutaryl CoA reductase wherein an amino acid at the 10th position in an Sα2 amino acid sequence is an amino acid other than alanine (A), an amino acid at the 1st position from carboxy terminus in the DKK region of the HMG-CoA binding site is an amino acid other than proline (P), an amino acid at the 1st position in an Lα2 amino acid sequence is an amino acid other than alanine (A), an amino acid at the 6th position in an Lα2 amino acid sequence is an amino acid other than glutamic acid (E), is increased.

Further, an activity of the hydroxymethylglutaryl CoA reductase of the present invention is increased compared to a hydroxymethylglutaryl CoA reductase wherein an amino acid at the 10th position in an Sα2 amino acid sequence is alanine (A), an amino acid at the 1st position from carboxy terminus in the DKK region of the HMG-CoA binding site is proline (P), an amino acid at the 1st position in an Lα2 amino acid sequence is alanine (A), an amino acid at the 5th position in an Lα2 amino acid sequence is isoleucine (I), an amino acid at the 6th position in an Lα2 amino acid sequence is glutamic acid (E), and amino acids other than those listed above are identical with the hydroxymethylglutaryl CoA reductase. That is to say, the activity of the hydroxymethylglutaryl CoA reductase wherein an amino acid at the 10th position in an Sα2 amino acid sequence is an amino acid other than alanine (A), an amino acid at 2nd position in amino acid sequence from amino terminus of Lα2 amino acid sequence to amino terminus of HMGR is an amino acid other than proline (P), an amino acid at the 1st position in an Lα2 amino acid sequence is an amino acid other than alanine (A), an amino acid at the 5th position in an Lα2 amino acid sequence is an amino acid other than isoleucine (I), an amino acid at the 6th position in an Lα2 amino acid sequence is an amino acid other than glutamic acid (E), is increased.

The term "activity of hydroxymethylglutaryl CoA reductase" as used herein basically means an activity capable of reducing HMGCoA so as to convert to mevalonic acid (MVA). However, a method for measuring activity is not limited to a method for measuring production of mevalonic acid, but includes a method for measuring various terpenoids in a downstream of the mevalonate pathway. For example, as described in Examples, the activity of hydroxymethylglutaryl CoA reductase can be determined by measuring the accumulation of squalene.

The hydroxymethylglutaryl CoA reductase of the present invention can be obtained by means of known genetic recombination techniques, and the like. For example, mRNA of yeast is obtained, and a gene of hydroxymethylglutaryl CoA reductase is amplified by PCR using appropriate primers. The obtained gene is inserted into an appropriate vector, and gene sequences thereof are determined. If (a) the amino acid at the 10th amino acid in an Sα2 amino acid sequence is alanine, (b) the amino acid at the 1st position from carboxy terminus in the DKK region of the HMG-CoA binding site is proline (P), (c) the amino acid at the 1st position in an Lα2 amino acid sequence is alanine (A), and (d) the amino acid at the 6th position in an Lα2 amino acid sequence is glutamic acid (E), the gene encoding the hydroxymethylglutaryl CoA reductase of the present invention can be obtained by substituting the above amino acids with different amino acids. Further, if (e) an amino acid at the 7th position in an Sα2 region is isoleucine, (f) an amino acid at the 5th position in an Lα2 region is isoleucine, and (g) an amino acid at the 6th position in an Sα2 region is alanine, the above amino acids may be substituted with different amino acids. The hydroxymethylglutaryl CoA reductase of the present invention can be obtained by inserting the obtained gene into a host such as yeast, and expressing the same.

Furthermore, a gene encoding the hydroxymethylglutaryl CoA reductase of the present invention can be synthesized by means of the known method for synthesizing genes, such as a method of Khorana et al. (Gupta et al., 1968), a method of Narang et al. (Scarpulla et al., 1982), or a method of Rossi et al. (Rossi et al., 1982). Then, the hydroxymethylglutaryl CoA reductase of the present invention can be obtained by expressing the synthesized gene.

The hydroxymethylglutaryl CoA reductase of the present invention is preferably (1) a hydroxymethylglutaryl CoA reductase consisting of a polypeptide comprising the 514th to 1022nd amino acids in the amino acid sequence of SEQ ID NO: 1. A polypeptide consisting of the 514th to 1022nd amino acids in the amino acid sequence of SEQ ID NO: 1 exhibits an excellent activity of hydroxymethylglutaryl CoA reductase, as described in the Examples. Thus, the polypeptide comprising the 514th to 1022nd amino acids in the amino acid sequence of SEQ ID NO: 1 equally exhibits an excellent activity of hydroxymethylglutaryl CoA reductase. For example, the polypeptides comprising the 514th to 1022nd amino acids in the amino acid sequence of SEQ ID NO: 1, for example, includes a fusion protein wherein a glutathione-S-transferase (GST) or His Tag is fused to an N terminus or C terminus side of the polypeptide consisting of the 514th to 1022nd amino acids, in order to increasing an expression level of hydroxymethylglutaryl CoA reductase. The fusion protein does not interfere with function of hydroxymethylglutaryl CoA reductase, and, for example, the fusion protein can be easily purified.

The hydroxymethylglutaryl CoA reductase of the present invention is preferably (2) a hydroxymethylglutaryl CoA reductase consisting of a polypeptide comprising amino acids wherein one or multiple amino acids are deleted, substituted, inserted, and/or added in the 514th to 1022nd amino acids of the amino acid sequence of SEQ ID NO: 1, and exhibits hydroxymethylglutaryl CoA reductase activity.

The term "amino acids wherein one or multiple amino acids are deleted, substituted, inserted, and/or added in the amino acid sequence" as used herein means that the amino acids are modified, for example, by substituting amino acid(s). The number of the modified amino acids is preferably 1 to 30, more preferably 1 to 10, more preferably 1 to 5, most preferably 1 to 2. As examples of modified amino acid sequences of mutant peptides, there may be mentioned an amino acid sequence having one or multiple (preferably 1, 2, 3, or 4) conservative substitutions.

The term "conservative substitution" as used herein means that one or multiple amino acid residues contained in a protein are replaced with different amino acids having similar chemical properties. As the conservative substitution, there may be mentioned, for example, a substitution of a hydrophobic residue for another hydrophobic residue, or a substitution of a polar residue for another polar residue having the same charge. Amino acids which have similar chemical properties and can be conservatively substituted with each other are known to those skilled in the art. More particularly, as nonpolar (hydrophobic) amino acids, there may be mentioned, for example, alanine, valine, isoleucine, leucine, proline, tryptophan, phenylalanine, or methionine. As polar (neutral) amino acids, there may be mentioned, for example, glycine, serine, threonine, tyrosine, glutamine, asparagine, or cysteine. As basic amino acids having a positive charge, there may be mentioned, for example, arginine, histidine, or lysine. As acidic amino acids having a negative charge, there may be mentioned, for example, aspartic acid or glutamic acid.

In the hydroxymethylglutaryl CoA reductase of the present invention, four or more substitutions (mutations), preferably five or more substitutions (mutations), more preferably six or more substitutions (mutations), most preferably seven or more substitutions (mutations) selected from the group consisting of: (a) the substitution (mutation) with an amino acid other than alanine (A) at the 10th position in an S$\alpha$2 amino acid sequence, (b) the substitution (mutation) with an amino acid other than proline (P) at the 1st position from the carboxy terminus in the DKK region of the HMG-CoA binding site (at the 2nd position in an amino acid sequence from the amino terminus of an L$\alpha$2 amino acid sequence to an amino terminus of HMGR), (c) the substitution (mutation) with an amino acid other than alanine (A) at the 1st position in an L$\alpha$2 amino acid sequence, (f) the substitution (mutation) with an amino acid other than isoleucine (I) at the 5th position in an L$\alpha$2 amino acid sequence, (d) the substitution (mutation) with an amino acid other than glutamic acid (E) at the 6th position in an L$\alpha$2 amino acid sequence, (g) the substitution (mutation) with an amino acid other than alanine (A) at the 6th position in an S$\alpha$2 amino acid sequence, and (e) the substitution (mutation) with an amino acid other than isoleucine (I) at the 7th position in an S$\alpha$2 amino acid sequence, are aggressive substitutions (mutations) in order to improve the activity of hydroxymethylglutaryl CoA reductase. However, the above conservative substitution is for maintaining the activity of hydroxymethylglutaryl CoA reductase, and thus, those skilled in the art can easily conduct it.

The hydroxymethylglutaryl CoA reductase of the present invention is preferably (3) a hydroxymethylglutaryl CoA reductase consisting of a polypeptide comprising amino acids having the homology of 80% or higher with the 514th to 1022nd amino acids in the amino acid sequence of SEQ ID NO: 1; and exhibiting hydroxymethylglutaryl CoA reductase activity.

The hydroxymethylglutaryl CoA reductase of the present invention is preferably (1) a hydroxymethylglutaryl CoA reductase consisting of an amino acid sequence of SEQ ID NO: 1. The polypeptide consisting of the amino acid sequence of SEQ ID NO: 1 exhibits an excellent hydroxymethylglutaryl CoA reductase activity, as shown in Examples.

The hydroxymethylglutaryl CoA reductase of the present invention is preferably (2) a hydroxymethylglutaryl CoA reductase consisting of a polypeptide consisting of amino acids wherein one or multiple amino acids are deleted, substituted, inserted, and/or added in the amino acid sequence of SEQ ID NO: 1, and exhibits hydroxymethylglutaryl CoA reductase activity.

The term "amino acids wherein one or multiple amino acids are deleted, substituted, inserted, and/or added in the amino acid sequence" as used herein means that the amino acids are modified, for example, by substituting amino acid(s), as mentioned above. For example, even if the 1st to 513th amino acids in the hydroxymethylglutaryl CoA reductase consisting of amino acids of the SEQ ID NO: 1 are deleted, the deleted hydroxymethylglutaryl CoA reductase can exhibit hydroxymethylglutaryl CoA reductase activity.

Therefore, in particular, the 1st to 513th amino acids may have deletion, substitution, or insertion, as long as the deletion, substitution, or insertion does not inhibit the hydroxymethylglutaryl CoA reductase activity.

The hydroxymethylglutaryl CoA reductase of the present invention is (3) a hydroxymethylglutaryl CoA reductase consisting of a polypeptide consisting of amino acids having the homology of preferably 80% or higher, more preferably 90% or higher, most preferably 95% or higher with the amino acid sequence of SEQ ID NO: 1; and exhibits hydroxymethylglutaryl CoA reductase activity. The term "homology" as used herein means an identity of an amino acid sequence.

According to a preferable embodiment of the hydroxymethylglutaryl CoA reductase of the present invention, it does not contain a membrane-bound domain. It is known that the hydroxymethylglutaryl CoA reductase consists of a membrane-bound domain (transmembrane domain), a linker region, and an active domain, for example, Non-patent literature 5 and the like disclose the membrane-bound domain of *S. cerevisiae*.

The term "not contain a membrane-bound domain" as used herein means the case that "not contain a membrane-bound domain together with a part of linker region" in addition to the case that "not contain a membrane-bound domain only". In the amino acid sequence of SEQ ID NO: 1, the membrane-bound domain is the 1st to 513th amino acid sequence thereof.

[2] Polynucleotide

The polynucleotide of the present invention is not particularly limited, so long as it is a polynucleotide encoding the hydroxymethylglutaryl CoA reductase of the present invention. That is to say, there may be mentioned a polynucleotide encoding the hydroxymethylglutaryl CoA reductase, wherein (a) an amino acid at the 10th position in an S$\alpha$2 amino acid sequence is an amino acid other than alanine (A), (b) an amino acid at the 1st position from the carboxy terminus in the DKK region of the HMG-CoA binding site (an amino acid at the 2nd position in an amino acid sequence from the amino terminus of L$\alpha$2 amino acid sequence to the amino terminus of HMGR) is an amino acid other than proline (P), (c) an amino acid at the 1st position in an L$\alpha$2 amino acid sequence is an amino acid other than alanine (A), and (d) an amino acid at the 6th position in an L$\alpha$2 amino acid sequence is an amino acid other than glutamic acid (E). As the preferable polynucleotide of the present invention, there may be mentioned a polynucleotide encoding the hydroxymethylglutaryl CoA reductase comprising one or more amino acids selected from the group of (e) an amino acid at the 7th position in an S$\alpha$2 region is an amino acid other than isoleucine (I), (f) an amino acid at the 5th position in an L$\alpha$2 region is an amino acid other than isoleucine (I), and (g) an amino acid at the 6th position in an S$\alpha$2 region is an amino acid other than alanine (A), in addition to the above amino acids (a) to (d).

Specifically, it may include a polynucleotide comprising a sequence consisting of the nucleotide sequence of SEQ ID NO: 2, or a polynucleotide comprising a sequence consisting of the 1540th to 3066th nucleotides in the nucleotide sequence of SEQ ID NO: 2.

Further, it may include a polynucleotide which hybridizes under stringent conditions to the polynucleotide comprising a sequence consisting of the nucleotide sequence of SEQ ID NO: 2, or the polynucleotide comprising a sequence consisting of the 1540th to 3066th nucleotides in the nucleotide sequence of SEQ ID NO: 2, and exhibits hydroxymethylglutaryl CoA reductase activity. In this connection, the term "polynucleotide" as used herein includes both DNA and RNA.

The term "stringent conditions" as used herein means conditions wherein two nucleotides are hybridized only when a homology between two nucleotide sequences is 90% or more, preferably 95% or more, more preferably 97% or more. Specifically, for example, the "stringent conditions" includes the following condition. Hybridization is carried out at 65° C. overnight, a washing is carried out using 2×SSC for 5 minutes in order to prevent a non-specific reaction. Then, a washing using 0.2×SSC containing 0.1% SDS at 65° C. for 30 minutes is repeated twice. The composition of 2×SSC is 0.3 mol/L NaCl and 30 mmol/L citric sodium (pH7.0).

[3] Microorganism

The microorganism of the present invention has the polynucleotide of the present invention. That is to say, it is not limited, so long as it includes the polynucleotide of the present invention therein, but it includes, for example, an *Escherichia coli*, *Bacillus subtilis*, actinomycete, baker's yeast, and *Neurospora crassa*.

[4] Vector

The vector of the present invention comprises a DNA having the polynucleotide of the present invention. That is to say, the vector of the present invention is not particularly limited, so long as it comprises the polynucleotide of the present invention. As the vector, there may be mentioned, for example, a vector obtained by introducing the polynucleotide of the present invention into a known vector appropriately selected in accordance with a host cell to be used.

As an expression vector, an expression vector which can autonomously replicate or can be inserted into a chromosome in a host such as *Escherichia coli* and baker's yeast, and can express an exogenous protein with high efficiency, is preferable. Further, the expression vector for expressing the above polynucleotide is preferably a recombinant vector which can autonomously replicate in a microorganism and is composed of a promoter, a ribosomal binding sequence, the above DNA, and transcription termination sequence. Furthermore, it may contain a promoter regulation gene.

More specifically, as an example of the expression vector, there may be mentioned, for example, pBTrp2, pBTac1, and pBTac2 (Boehringer Mannheim), pKK233-2 (Pharmacia), pSE280 (Invitrogen), pGEMEX-1 (Promega), pQE-8 (QIAGEN), pQE-30 (QIAGEN), pKYP10 (Japanese Unexamined Patent Publication (Kokai) No. 58-110600), pKYP200 [Agricultural Biological Chemistry, 48, 669(1984)], pLSA1 [Agric. Biol. Chem., 53, 277(1989)], pGEL1 [Proc. Natl. Acad. Sci. USA, 82, 4306(1985)], pBluescriptII SK+, pBluescriptII SK (−)(Stratagene), pTrS30 (FERMBP-5407), pTrS32(FERM BP-5408), pGEX (Pharmacia), pET-3 (Novagen), pTerm2 (U.S. Pat. Nos. 4,686,191, 4,939,094, 5,160,735), pSupex, pUB110, pTP5, pC194, pUC18 [gene, 33, 103(1985)], pUC19 [Gene, 33, 103(1985)], pSTV28 (Takara), pSTV29 (Takara), pUC118 (Takara), pPA1 (Japanese Unexamined Patent Publication (Kokai) No. 63-233798), pEG400 [J. Bacteriol., 172, 2392 (1990)].

A promotor is not limited, as long as a gene can express in the cells of a host such as *Escherichia coli* and baker's yeast. For example, there may be mentioned, a promotor derived from *Escherichia coli*, phage, or the like (such as trp promotor (Ptrp), lac promotor (Plac), $P_L$ promotor, $P_R$ promotor, or $P_{SE}$ promotor), SPO1 promotor, SPO2 promotor, penP promotor, or the like. Further, artificially-modified (artificially-designed) promotors such as a promotor wherein the two Ptrps are connected in series (Ptrpx2), tac promotor, letI promotor, or lacT7 promotor, can be used. Among the above promotors of the present invention, a promotor capable of constantly-expressing a gene of interest regardless of tissues, i.e., a constitutive promotor is more preferable. As the constitutive promotor, there may be mentioned promotors of alcohol dehydrogenase I gene (ADH1), elongation factor TF-1α gene (TEF1), phosphoglycerate kinase gene (PGK1), Triosephosphate isomerase gene (TPI1), Triosephosphate dehydrogenase gene (TDH3), or pyruvate kinase gene (PYK1).

[5] Transformant

The transformant of the present invention is also not particularly limited, as long as it contains the polynucleotide of the present invention. For example, it includes a transformant wherein the polynucleotide of the present invention is inserted into a chromosome in a host, or a transformant comprising a vector containing the polynucleotide of the present invention. Further, it includes a transformant expressing the polypeptide of the present invention, or a transformant not-expressing the polypeptide of the present invention. The transformant of the present invention may be obtained, for example, by transforming a desired host cell with the vector of the present invention, or the polynucleotide of the present invention per se.

The host cell is not particularly limited. A strain which is easy to handle, such as *Escherichia coli*, *Bacillus subtilis*, actinomycete, yeast, and *Neurospora crassa* is preferable, but, insect cells, plant cells, animal cells, or the like can be used. However, yeast is most preferable. As the most preferable yeast strain, there may be mentioned sake yeast. Specifically, sake yeast strain K7 or K701 is more preferable. The strain K701 is a non-foaming mutant strain bred from wild-type strain K7. However, the strain K701's characters other than the above characters are the same as K7.

[6] Method for Preparing Terpenoid and Method for Preparing Squalene

A terpenoid or squalene can be prepared by culturing the host cell transformed with the expression vector. Regarding the yeast, the yeast may be cultured in a conventional YPD medium and the like. For example, the yeast wherein a gene is introduced by a homologous recombination, or the yeast having the expression vector, is precultured. Then, the precultured yeast is inoculated to a YPD medium or the like, and it is cultured for about 24 to 240 hours, preferably about 72 to 120 hours. The terpenoid or squalene which is secreted into the medium can be used as it is, or after a purification by the known method. The terpenoid or squalene which is accumulated in cells is obtained as follows. They can be extracted using appropriate organic solvents after cell disruption through a conventional technique such as an enzyme treatment of cells or an ultrasonic wave, and then can be purified using centrifugation or various chromatography.

According to the present invention, various terpenoid compounds can be effectively produced by improving the HMGR activity in an upstream of the terpenoid biosynthesis pathway. In particular, squalene, and various sterol compounds such as ergosterol or cholesterol which is biologically synthesized via squalene can be effectively produced.

EXAMPLES

The present invention will now be further illustrated by, but is by no means limited to, the following Examples.

Example 1: Cloning of HMGR Gene

In this Example, the HMGR gene was cloned. The HMGR gene was obtained from an ML-236B resistance strain, which was obtained by culturing a yeast (*Saccharomycopsis fibuligera*) using a medium containing ML-236B (hereinafter, the HMGR gene obtained from the ML-236B resistance strain is sometimes referred to as "ADK4653" or "ADK4653 gene.").

(1) Cloning of Full Length HMGR Gene from ML-236B Resistance Strain

The HMGR gene was amplified by a PCR method using genome DNA of the ML-236B resistance strain as a template. The genome DNA was prepared according to a standard method, after a digestion of cell walls using Zymolyase 20T (Kirin Kyowa Foods), and then the genome DNA was purified using a NucleoBond AXG 20 column (MACHEREY-NAGEL). PCR was carried out using PrimeSTAR Max DNA Polymerase (Takara Bio Inc.), the following primers (SEQ ID NO: 3 and SEQ ID NO: 4), and thermal cycler (TP240, Takara Bio Inc.).

```
                                        (SEQ ID NO: 3)
5'-AATCAACTGGTACCCGGGATGTTTAGCCTTAGTAATTATGT-3'

(SEQ ID NO: 4)
5'-TTAGTTAACCTCTAGAGCTCTTAAGATTTGATACAGATCTTTGA-3'
```

PCR was performed by repeating 35 cycles of a 3 step reaction (98° C. for 10 seconds, 55° C. for 5 seconds, and 72° C. for 15 seconds). A homologous sequence of a cloning site of a vector was added to the 5' end of the primers. PCR product was examined by an agarose gel electrophoresis as to whether or not a desired size of DNA is contained and non-specific bands are contained, and then purified using a NucleoSpin Gel and PCR Clean-up column (MACHEREY-NAGEL).

(2) Construction of Expression Vector

In this cloning, a vector pAUR123 for expression (Takara Bio Inc.) was used. The vector was treated with a restriction enzyme SacI (Takara Bio Inc.) and restriction enzyme SmaI (Takara Bio Inc.). Subsequently, a DNA fragment of interest was cut out by an agarose gel electrophoresis, and then purified using a NucleoSpin Gel and PCR Clean-up column (MACHEREY-NAGEL). The HMGR gene was reacted using GemeArt Seamless Cloning and Assembly Enzyme Mix (Invitrogen) in accordance with a manual, and cloned into a vector. The reaction mixture was directly used for a transformation of *E. coli* competent cells (HST08, Takara Bio Inc.). It was confirmed that the gene of interest was introduced into the positive clones by a colony PCR, and subsequently plasmids of positive clones were prepared using NucleoSpin Plasmid (MACHEREY-NAGEL). The colony PCR was carried out by using TaKaRa Ex Taq (Takara Bio Inc.), and primers (SEQ ID NO: 5 and SEQ ID NO: 6). The infinitesimal quantity of *E. coli* colonies obtained by transformation were picked up by a chip or wooden pick, and suspended in a PCR reaction solution. PCR reaction was carried out by a denaturation treatment of 94° C. for 1 minute, a reaction step of 30 cycles of 98° C. for 10 seconds, 61° C. for 30 seconds, 72° C. for 3 minutes, and an elongation reaction of 72° C. for 3 minutes. After PCR, the presence or absence of the insertion was examined by an agarose gel electrophoresis so as to obtain the expression vector for full length HMGR of an ML-236B resistance strain.

```
                                        (SEQ ID NO: 1)
5'-TCTGCACAATATTTCAAGC-3'
```

```
                                        (SEQ ID NO: 6)
5'-TTCGTTTTAAAACCTAAGAGTCAC-3'
```

(3) Cloning of Truncated HMGR (tHMGR) Gene

The truncated HMGR gene was amplified by a PCR method using genome DNA of the ML-236B resistance strain as a template. The genome DNA was prepared according to a standard method, and subsequently it was purified using a NucleoBond AXG 20 column (MACHEREY-NAGEL). PCR was performed by repeating 35 cycles of a 3 step reaction (98° C. for 10 seconds, 55° C. for 5 seconds, and 72° C. for 15 seconds) using PrimeSTAR Max DNA Polymerase (Takara Bio Inc.). The PCR primers of base sequences of SEQ ID NO: 7 and SEQ ID NO: 8 were used.

```
                                        (SEQ ID NO: 7)
5'-AATCAACTGGTACCCGGGATGTCTCAACGTCTTAGCAAGGCTAT
T-3'

(SEQ ID NO: 8)
5'-TTAGTTAACCTCTAGAGCTCTTAAGATTTGATACAGATCTTTGA-3'
```

A homologous sequence of a cloning site of the vector used for cloning was added to a 5' end of the primers.

The PCR product was purified using a NucleoSpin Gel and PCR Clean-up column (MACHEREY-NAGEL) after confirming a presence of PCR product by an agarose gel electrophoresis. A vector pAUR123 (Takara Bio Inc.) for expression was used for cloning. The PCR product was reacted using GemeArt Seamless Cloning and Assembly Enzyme Mix (Invitrogen). The reaction mixture was directly used for a transformation of *E. coli* competent cells (HST08, Takara Bio Inc.). It was confirmed that the gene of interest was introduced into the positive clones by a colony PCR, and subsequently plasmids of positive clones were prepared using NucleoSpin Plasmid (MACHEREY-NAGEL). It was confirmed that errors caused by PCR reaction are not contained in the cloned truncated HMGR gene by a sequencing analysis. The sequencing analysis was carried out using the purified plasmid as a template, and the plasmid was analyzed using the primers of SEQ ID NO: 5 and SEQ ID NO: 6, and a DNA sequencer (Applied Biosystems, 3730xl), so as to obtain an expression vector of the truncated HMGR of ML-236B resistance strain (hereinafter, sometimes referred to as a "ADK4653_tHMGR").

Comparative Example 1

In this Comparative Example, the truncated HMGR (tHMGR) gene was cloned and formed sake yeasts.

The procedure described in Example 1(3) was repeated, except that a sake yeast (*Saccharomyces cerevisiae* K701 strain) was used instead of the ML-236B resistance strain, and the primers of SEQ ID NO: 9 and SEQ ID NO: 10 were used as primers, to construct an expression vector of a truncated HMGR of sake yeast (hereinafter, sometimes referred to as a "K701_tHMGR").

```
                                        (SEQ ID NO: 9)
5'-AATCAACTGGTACCCGGGATGGACCAATTGGTGAAAACT-3'

(SEQ ID NO: 10)
5'-TTAGTTAACCTCTAGAGCTCTTAGGATTTAATGCA-3'
```

Example 2

In this Example, a transformant of yeast was obtained by using the vector obtained in Example 1(2). A production of mevalonic acid and a production of squalene or ergosterol were carried out by using the resulting transformant.

(1) Transformation of Yeast

The sake yeast (*Saccharomyces cerevisiae* K701 strain) was transformed by using the full length HMGR expression vector obtained in Example 1(2). The vector was preliminarily digested with a restriction enzyme EcoO65I (BstEII, BstPI) (Takara Bio Inc.) at one site in a resistance marker gene, and the linear vector gene is introduced by a homologous recombination. Specifically, the homologous recombination occurred at a susceptible gene site of the host yeast which shares homology with an Aureobasidin resistant gene (AUR-C) that is a resistance marker of the vector, so that the vector gene was inserted into the susceptible gene site of the host yeast. The transformation of yeast was carried out in accordance with a standard method, i.e., lithium acetate method using a Frozen-EZ Yeast Transformation II (ZYMO RESARCH). Transformants were selected by using a YPD medium containing 0.5 µg/mL of antibiotic (Aureobasidin A, Takara Bio Inc.). It was confirmed that the gene of interest was introduced into the obtained clones by a colony PCR. In the colony PCR, Tks Gflex DNA Polymerase (Takara Bio Inc.), and primers (SEQ ID NO: 5 and SEQ ID NO: 6) were used. The infinitesimal quantity of the yeast colony was picked up and suspended in an enzyme solution for cell-wall digestion (Zymolyase 20T, Kirin Kyowa Foods, 3 mg/mL, pH7.4), and then the suspension was reacted at 37° C. for 15 minutes to digest the cell wall thereof. PCR reaction was carried out using the enzyme-treated solution as a template DNA. PCR reaction was carried out by a denaturation treatment of 94° C. for 1 minute, a reaction step of 30 cycles of 98° C. for 10 seconds, 60° C. for 15 seconds, 68° C. for 3 minutes, and an elongation reaction of 68° C. for 90 seconds. After PCR, the presence or absence of the insertion was examined by an agarose gel electrophoresis.

(2) Examination for Production of Mevalonic Acid, Squalene or Ergosterol

ADK4653 gene was constitutively expressed by the constitutive expression promotor (promotor of ADH1 gene) of the expression vector pAUR123 (Takara Bio Inc.). The mevalonate pathway was improved by an overexpression of an ADK4653 gene which was introduced by the transformation in addition to the expression of the inherent HMGR gene of sake yeast. The improvement of the mevalonate pathway was confirmed by measuring mevalonic acid, squalene or ergosterol, which are metabolic products in the mevalonate pathway. In a control study, a transformant obtained by a transformation using a vector in which the insert was not contained was used as a control.

A culture was carried out using a 500 mL conical flask equipped with a baffle. 1% by volume of yeast cells which were precultured for 24 hours was added to 50 mL of a YPD medium (containing 5% glucose), and the whole was cultured at 28° C. while rotating at 250 rpm. Samples were collected at predetermined times. The quantitative determinations of mevalonic acid, squalene, and ergosterol were carried out as follows.

Quantitative Determination of Mevalonic Acid

A concentration of mevalonic acid, which is produced and secreted to the medium, is measured. A supernatant of culture liquid obtained by centrifugation was directly analyzed by HPLC. As an HPLC system, LaChrom (Column Oven L-2300, Pump L-2130, Autosampler L-2200, UV Detector L-2400; HITACHI) and a column (Thermo SCIENTIFIC, AQUASIL C18) were used. An isocratic (water: trimethylamine:acetic acid=1000:1:1) was used as an eluent. Column temperature and flow rate were set up 40° C. and 1.0 mL/min, respectively, and the mevalonic acid was analyzed by UV detection (210 nm).

Quantitative Determinations of Squalene and Ergosterol

Squalene and ergosterol were measured by disrupting yeast cells and extracting the same using chloroform and methanol. Two mL of culture liquid was centrifuged and a supernatant was removed. Subsequently, 0.6 mL of zirconia beads for disruption (NIKKATO CORPORATION, YTZ ball, φ0.5 mm) and 0.4 mL of methanol were added to the yeast cells, and the yeast cells were disrupted for 5 minutes at 3200 r/min by a beads crusher (TAITEC, uT-12). 0.8 mL of chloroform was added to the crushed liquid, and the whole was stirred upside down so as to be homogeneous. The mixture was suspended by a sonication for 5 minutes, and then centrifuged at 16000 rpm, for 5 min to collect an organic layer. The sample was subjected to HPLC analysis after a treatment of filter (ADVANTEC, DISMIC-13HP). As an HPLC system, a system of JASCO Corporation (JASCO Intelligent HPLC Pump 880-PU, Ternary Gradient Umit 880-02, Intelligent UV/VIS Detector 870-UV, SSC-2100 (Senshu Scientific), GL Sciences Degassing Unit DG660B) and a column (SIGMA-ALDRICH, SUPELCOSIL LC-18) were used. An isocratic (acetonitrile:THF=8:2) was used as an eluent. Column temperature and flow rate were set up 30° C. and 1.0 mL/min, respectively, and the squalene and ergosterol were analyzed by UV detection (220 nm).

The results of production of mevalonic acid are shown in FIG. 4. In the host wherein the ADK4653_HMGR was expressed, mavalonic acid of 2 to 2.8 times that of the control (185-355 mg/L) was accumulated.

Further, the results of productions of squalene and ergosterol are shown in FIG. 5. An amount of ergosterol in sake yeast wherein ADK4653_HMGR was expressed was not significantly changed. On the other hand, a production amount of squalene was significantly increased. That is, an enhancing effect of a mevalonate pathway was confirmed.

In connection to this, the term "no insert" in FIGS. 4 and 5 means a host in which a pAUR123 vector without an exogenous gene was introduced and the exogenous gene was not expressed. Further, the term "ADK" means "ADK4653." (The same is true on the following figures and tables.)

Example 3

In this Example, transformants of yeast were obtained using the vector obtained in Example 1(3). Then, squalene or ergosterol was produced using the transformants.

Specifically, the procedures described in Example 2(1) and 2(2) were repeated, except that the ADK4653_tHMGR expression vector was used instead of the ADK4653_HMGR expression vector. The results are shown in FIG. 6.

Comparative Example 2

In this Comparative Example, a production of squalene was examined using the K701_tHMGR expression vector obtained in Comparative Example 1. The procedure described in Example 3 was repeated, except that the K701_tHMGR expression vector was used instead of the ADK4653_tHMGR expression vector (The culture term is 5 days.). The results are shown in FIG. 6.

As shown in FIG. 6, when the ADK4653_tHMGR was expressed instead of the ADK4653_HMGR, squalene production of 12 times that of ADK4653_HMGR was observed.

The squalene production amount in the medium reached 1.66 g/L, and thus the production amount per dried yeast cells was 102 mg/g (10.2%). On the other hand, in the K701_tHMGR in Comparative example 2, an enhancing effect of squalene production was not observed.

A comparison of amino acid sequences of the ADK4653_HMGR, sake yeast (*Saccharomyces cerevisiae* K7 strain) HMGR, and human (*Homo sapiens*, AF273765) HMGR is shown in FIG. 7-1 and FIG. 7-2. As shown in FIG. 7-1 and FIG. 7-2, in the HMGR obtained from sake yeast, the 10th amino acid in an Sα2 amino acid sequence of HMGR is alanine. While on the other hand, that of ADK4653_HMGR is serine. Further, in the HMGR obtained from sake yeast, the 2nd amino acid from the amino terminus of an Lα2 amino acid sequence to the amino terminus of HMGR is proline. While on the other hand, that of ADK4653_HMGR is alanine. Furthermore, in the HMGR obtained from sake yeast, the 1st amino acid in an Lα2 region is alanine, the amino acid in an Lα2 region is isoleucine, and the 6th amino acid in an Lα2 region is glutamic acid. While on the other hand, those of ADK4653_HMGR are serine, threonine, and asparagine, respectively.

In connection to this, the amino acid sequences of a truncated HMGR region of the sake yeast (*Saccharomyces cerevisiae* K7 strain) and the sake yeast (*Saccharomyces cerevisiae* K701 strain) are identical.

Example 4

In this Example, a time course of the squalene production amount of ADK4653_tHMGR was examined. The procedure described in Example 3 was repeated, except that the culture term was 3 days, 4 days, 5 days, 6 days, 7 days, or 10 days; or 3 days, 5 days, 7 days, or 10 days, to measure a squalene production amount. Further, changes of the weight of cells were also measured simultaneously. The results are shown in FIG. 8.

In the yeast wherein ADK4653_tHMGR was expressed, an excellent squalene production amount was observed, in comparison with the control (No insert). Further, the squalene amount was flat on and after 3 days wherein the cells were in a stationary phase, an adequate amount of squalene was obtained by a culture within 3 days. On the other hand, there is no difference between an amount of ergosterol of yeast in which the truncated gene (ADK4653_tHMGR) was expressed and that of the control (No insert).

Comparative Example 3

In this Comparative Example, the amount of squalene production was examined by substituting the 1st amino acid serine in an Lα2 amino acid sequence by alanine; or substituting the 1st amino acid serine in an Lα2 amino acid sequence by alanine and the 5th amino acid threonine in an Lα2 amino acid sequence by isoleucine in the ADK4653_tHMGR expression vector obtained in Example 1(3). In addition, the K701_tHMGR was used as a control (the same is true on the following Comparative Examples 4 to 6.).

The amount of squalene production was measured in accordance with a method described in Example 2(2). A culture was carried out using a conical flask equipped with a baffle. Precultured yeast cells was added to 50 mL of a YPD medium (containing 5% glucose), and the whole was cultured at 28° C. while rotating at 250 rpm. After 2 days of culturing, the cultured yeast cells were collected, and the amount of squalene production was measured.

Using the ADK4653_tHMGR expression vector as a template, the above amino acid substitutions were introduced thereinto. Specifically, an S820A vector wherein the 1st amino acid serine in an Lα2 amino acid sequence was substituted by alanine was prepared, and an S820A/T824I vector wherein the 1st amino acid serine in an Lα2 amino acid sequence was substituted by alanine and the 5th amino acid threonine in an Lα2 amino acid sequence was substituted by isoleucine was prepared. The resulting S820A vector or S820A/T824I vector was introduced into the sake yeast as a host, so as to obtain an S820A strain, or an S820A/T824I strain wherein the substituted ADK4653_tHMGRs were overexpressed, respectively. The enhancing effects of mevalonate pathways were compared by using an index as amounts of squalene productions of each strain. The results were shown in FIG. 9. The amounts of squalene production were shown as a relative value, and the relative value was determined when the amount of production of ADK4653_tHMGR wherein the substitutions were not introduced was regarded as 100%, on the basis of the production amount per culture medium (The same is true on the following FIGS. 10 to 16.).

In connection to this, the expression vectors were prepared using PrimeSTAR DNA Polymerase (Takara Bio Inc.) in accordance with a manual (PrimeSTAR Mutagenesis Basal Kit, product code:R046A). A plasmid to be mutation-introduced was diluted with sterile, distilled water, and added to a reaction solution so that the concentration became 2 pg/μL. The primers were added thereto so that the final concentration became 2 pg/μL. PCR was performed by repeating 40 cycles of a 3 step reaction (98° C. for 10 seconds, 55° C. for 15 seconds, and 72° C. for 45 seconds), and an amplified product with a desired size was confirmed by an agarose gel electrophoresis. Then, a transformation was carried out by adding 0.4 μL of the PCR reaction solution to 20 μL of competent cells (JM109, Takara Bio Inc.). Plasmids wherein mutation(s) were introduced were purified from the *E. coli* obtained by the transformation, and a nucleotide sequence of a structure gene encoding HMGR was analyzed. An accuracy of introduced mutation (introduction of mutation of interest, and absence of unintended error due to PCR) was verified by the analysis of the nucleotide sequence. A host i.e., sake yeast was transformed by the expression vector wherein the mutation(s) were introduced, and a squalene production was analyzed. As primers for introducing mutation(s), the following primers were synthesized and used (SEQ ID NO: 11, 12, 15, and 16).

When the 1st amino acid serine in an Lα2 amino acid sequence was substituted by alanine, the amount of squalene production was decreased. Further, the mutant wherein the two amino acids were substituted, hardly exhibits high productivity.

It was revealed that the serine and threonine present at the motif (Lα2) adjacent to the HMG-CoA binding site are important amino acid residues involved in a high productivity of squalene.

Mutated Enzyme (S820A)

```
                                               (SEQ ID NO: 11)
5'-GCCATTAACTGGACCAATGGTCGTGGTAAGAGT-3'

(SEQ ID NO: 12)
5'-GGTCCAGTTAATGGCAGCGGCTTTCTTATCAGT-3'
```

Mutated Enzyme (S820A/T824I)

```
                                              (SEQ ID NO: 15)
5'-GCCATTAACTGGATCAATGGTCGTGGTAAGAGT-3'

(SEQ ID NO: 16)
5'-GATCCAGTTAATGGCAGCGGCTTTCTTATCAGT-3'
```

Comparative Example 4

In this Comparative Example, the amount of squalene production was examined by substituting the 10th amino acid serine in an Sα2 amino acid sequence by alanine in the ADK4653_tHMGR expression vector obtained in Example 1(3). The culture was carried out by repeating the procedure of Comparative Example 3, and then the amount of squalene production was measured. The results were shown in FIG. 10. The mutant wherein the 10th amino acid serine was substituted by alanine, hardly exhibits high productivity.

Mutated Enzyme (S744A)

```
                                              (SEQ ID NO: 17)
5'-TGAAAAAAGCTTTCAATTCTACTTCTA-3'

(SEQ ID NO: 18)
5'-ATTGAAAGCTTTTTTCAACAAGTTTTG-3'
```

Comparative Example 5

In this Comparative Example, the amount of squalene production was examined by substituting the 818th amino acid alanine positioned between the HMG-CoA binding site and Lα2 by proline in the ADK4653_tHMGR expression vector obtained in Example 1(3). The culture was carried out by repeating the procedure of Comparative Example 3 except for a culture term of 3 days, and then the amount of squalene production was measured. The results were shown in FIG. 11. The mutant wherein the 818th amino acid serine was substituted by alanine, hardly exhibits high productivity.

Mutated Enzyme (A818P)

```
                                              (SEQ ID NO: 19)
5'-TGATAAGAAACCAGCTTCTATTAACTG-3'

(SEQ ID NO: 20)
5'-GCTGGTTTCTTATCAGTACAGTAGTTA-3'
```

Comparative Example 6

In this Comparative Example, the amount of squalene production was examined by substituting the 825th amino acid asparagine by glutamic acid in the ADK4653_tHMGR expression vector obtained in Example 1(3). The culture was carried out by repeating the procedure of Comparative Example 3 except for a culture term of 3 days, and then the amount of squalene production was measured. The results were shown in FIG. 12. The mutant wherein the 825th amino acid asparagine was substituted by glutamic acid, hardly exhibits high productivity.

Mutated Enzyme (N825E)

```
                                              (SEQ ID NO: 21)
5'-TGGACCGAAGGTCGTGGTAAGAGTATTG-3'
```

```
                                              (SEQ ID NO: 22)
5'-ACGACCTTCGGTCCAGTTAATAGAAGCG-3'
```

Example 5

In this Example, a mutated enzyme wherein mutations were introduced at 3 amino acid residues in an Sα2 region, 1 amino acid positioned between the HMG-CoA binding site and an Lα2, and 3 amino acid residues in an Lα2 region, was prepared using the K701_tHMGR expression vector obtained in Comparative Example 1, and the amount of squalene production was examined.

An introduction of mutations is explained in more detail below. In connection to this, the sequence numbers of the sake yeast (*Saccharomyces cerevisiae* K7 strain) as shown in FIG. 7-1 and FIG. 7-2 were used as the numbers for identifying the mutation position, in this Example. As mentioned above, the sake yeast (*Saccharomyces cerevisiae* K701 strain) was used in this Example, but the amino acid sequence of the active site (truncated HMGR region) of the K701 strain is identical with that of the sake yeast (*Saccharomyces cerevisiae* K7 strain). Thus, the sequence numbers of the K7 strain were used for identifying the mutation position.

As shown in FIG. 7-1 and FIG. 7-2, the amino acid sequence in an Sα2 region of the sake yeast (*Saccharomyces cerevisiae* K701 strain) is "EEGQNAIKKAFN" and the amino acid sequence from HMG-CoA binding site to an Lα2 region thereof is "DKKPAAINWIE".

The amino acid substitution mutations were introduced into the K701_tHMGR expression vector, so that the amino acid sequence of an Sα2 region becomes "EEGQN-LLKKSFN" and the amino acid sequence from HMG-CoA binding site to an Lα2 region thereof becomes "DKKAAS-INWTN". That is to say, alanine (the 772 position) of the 6th position of an Sα2 region was substituted by leucine, isoleucine (the 773 position) of the 7th position of an Sα2 region was substituted by leucine, and alanine (the 776 position) of the 10th position of an Sα2 region was substituted by serine. Further, proline (the 850 position) existed at the 2nd position from the amino terminus of an Lα2 region to an amino terminus of HMGR, which is just behind the HMG-CoA binding site, was substituted by alanine, alanine (the 852 position) of the 1st position of an Lα2 region was substituted by serine, isoleucine (the 856 position) of the 5th position of an Lα2 region was substituted by threonine, and glutamic acid (the 857 position) of the 6th position of an Lα2 region was substituted by asparagine.

An introduction of the amino acid substitution mutations was carried out using the K701_tHMGR expression vector as a template. In accordance with the method of Comparative Example 3, the mutations were introduced in order by repeating the procedures using different primers, so that a vector, wherein the 7 amino acids were substituted, was constructed. As primers for introducing mutations, the following primers (SEQ ID NO: 23 to 32) were synthesized and used.

The constructed vector was introduced into the host, i.e. sake yeast so as to obtain a K701_Mutant strain. The enhancing effects of mevalonate pathways were compared by using an index as amounts of squalene productions of each strain. The amount of squalene production was measured in accordance with a method described in Example 2(2). A culture was carried out using a conical flask equipped with a baffle. Precultured yeast cells were added to 50 mL of a YPD medium (containing 5% glucose), and the whole was cultured at 28° C. while rotating at 250 rpm. After 2 days of culturing, the cultured yeast cells were collected, and the amount of squalene production was measured. In addition, the ADK4653_tHMGR and K701_tHMGR were used as controls. The results are shown in FIG. 13. A squalene production amount of the yeast expressing the mutated enzyme, wherein the 7 amino acids were substituted, was significantly increased, compared to that of K701_tHMGR. That is, the yeast exhibited the production amount similar to ADK4653_tHMGR.

It was revealed that the 7 amino acids existed in the neighborhood of the motif (Sα2) adjacent to the NADP(H) binding site and the motif (Lα2) adjacent to the HMG-CoA binding site are important amino acids involved in a high productivity of squalene, and the mevalonate pathway can enhance by expressing the mutated enzyme wherein the mutations are introduced.

Mutated Enzyme (K701_Mutant:A852S/I856T)

```
                                       (SEQ ID NO: 23)
5'-TCTATCAACTGGACCGAAGGTCGTGGTAAGAGT-3'

(SEQ ID NO: 24)
5'-GGTCCAGTTGATAGAAGCTGGTTTTTTGTCGGT-3'
```

Mutated Enzyme (K701_Mutant:A776S)

```
                                       (SEQ ID NO: 25)
5'-AAAAAATCATTTAACTCTACATCAAGA-3'

(SEQ ID NO: 26)
5'-GTTAAATGATTTTTTAATTTGCGTTTTG-3'
```

Mutated Enzyme (K701_Mutant:E857N)

```
                                       (SEQ ID NO: 27)
5'-TGGACCAATGGTCGTGGTAAGAGTGTC-3'

(SEQ ID NO: 28)
5'-ACGACCATTGGTCCAGTTGATAGAAGC-3'
```

Mutated Enzyme (K701_Mutant:P850A)

```
                                       (SEQ ID NO: 29)
5'-CGACAAAAAAGCCGCTTCTATCAACTG-3'

(SEQ ID NO: 30)
5'-GCGGCTTTTTTGTCGGTACAGTAGTTA-3'
```

Mutated Enzyme (K701_Mutant:A772L/I773L)

```
                                       (SEQ ID NO: 31)
5'-AAAACTTGTTGAAAAAATCATTTAACTC-3'

(SEQ ID NO: 32)
5'-TTTTCAACAAGTTTTGTCCCTCTTCTG-3'
```

Example 6

In this Example, the amount of squalene production was examined by substituting the 5th amino acid threonine in an Lα2 amino acid sequence by isoleucine in the ADK4653_tHMGR expression vector obtained in Comparative Example 1(3). The procedure described in Example 3 was repeated except that the following primers of SEQ ID NO: 13 and 14 were used as primers for introducing mutations, to obtain the T824I vector. The T824Ivector was introduced into sake yeast so as to obtain a T824I strain. The enhancing effects of mevalonate pathways were compared by using an index as amounts of squalene productions. The results are shown in FIG. 9. When the 5th amino acid threonine in an Lα2 amino acid sequence was substituted by isoleucine, the amount of squalene production was 50.3% with respect to that of ADK4653_tHMGR, but it was significantly high compared to that of K701_tHMGR.

Mutated Enzyme (T824I)

```
                                       (SEQ ID NO: 13)
5'-TCTATTAACTGGATCAATGGTCGTGGTAAGAGT-3'

(SEQ ID NO: 14)
5'-GATCCAGTTAATAGAAGCGGCTTTCTTATCAGT-3'
```

Examples 7 and 8

In this Example, the amount of squalene production was examined by substituting the 740th amino acid leucine by alanine, or substituting the 741st amino acid leucine by isoleucine in the ADK4653_tHMGR expression vector obtained in Example 1(3). The introduction of mutations was carried out in accordance with the method of Comparative Example 3 using the following primers. The culture was carried out by repeating the procedure of Comparative Example 3, and the amount of squalene production was measured. The results are shown in FIG. 14. As a result, when the 740th amino acid leucine was substituted by alanine, the amount of squalene production was 54.2% with respect to that of ADK4653_tHMGR, but it was significantly high compared to that of K701_tHMGR. Further, when the 741st amino acid leucine was substituted by isoleucine, the amount of squalene production was 18.8% with respect to that of ADK4653_tHMGR, but it was significantly high compared to that of K701_tHMGR Mutated Enzyme (L740A).

```
                                       (SEQ ID NO: 33)
5'-AAAACGCATTGAAAAAATCATTCAATTC-3'

(SEQ ID NO: 34)
5'-TTTTCAATGCGTTTTGACCTTCTTCAGTA-3'
```

Mutated Enzyme (L741I)

```
                                       (SEQ ID NO: 35)
5'-ACTTGATTAAAAAATCATTCAATTCTA-3'

(SEQ ID NO: 36)
5'-ATTTTTTAATCAAGTTTTGACCTTCTTCA-3'
```

Example 9

In this Example, the procedure described in Example 5 was repeated using the K701_tHMGR expression vector obtained in Comparative Example 1 except that 2 amino acid mutations were introduced into amino acid residues in an Sα2 region instead of 3 amino acid mutations, to prepare a mutated enzyme and the amount of squalene production was examined. (The numbers for identifying the mutation position are same as those of Example 5.

That is to say, the amino acid substitution mutations were introduced into the K701_tHMGR expression vector, so that the amino acid sequence of an Sα2 region becomes "EEGQNALKKSFN" and the amino acid sequence from HMG-CoA binding site to an Lα2 region thereof becomes "DKKAASINWTN". That is, isoleucine (the 773 position) of the 7th position of an Sα2 region was substituted by leucine, and alanine (the 776 position) of the 10th position of an Sα2 region was substituted by serine. Further, proline (the 850 position) existed at the 2nd position from the amino terminus of an Lα2 region to an amino terminus of HMGR, which is just behind the HMG-CoA binding site, was substituted by alanine, alanine (the 852 position) of the 1st position of an Lα2 region was substituted by serine, isoleucine (the 856 position) of the 5th position of an Lα2 region was substituted by threonine, and glutamic acid (the 857 position) of the 6th position of an Lα2 region was substituted by asparagine.

An introduction of the amino acid substitution mutations was carried out using the K701_tHMGR expression vector as a template. In accordance with the method of Comparative Example 3, the mutations were introduced in order by repeating the procedures using different primers, so that a vector, wherein the 6 amino acids were substituted, was constructed. As primers for introducing mutations, the primers (SEQ ID NO: 23 to 30) used in Example 5 and the following primers (SEQ ID NO: 37 to 38) were synthesized and used.

The constructed vector was introduced into the host, i.e. sake yeast so as to obtain a K701_Mutant2 strain. The enhancing effects of mevalonate pathways were compared by using an index as amounts of squalene productions of each strain. The amount of squalene production was measured in accordance with a method described in Example 2(2). A culture was carried out using a conical flask equipped with a baffle. Precultured yeast cells were added to a YPD medium (containing 5% glucose), and the whole was cultured at 28° C. while rotating at 250 rpm. After 2 days of culturing, the cultured yeast cells were collected, and the amount of squalene production was measured. In addition, the ADK4653_tHMGR and K701_tHMGR were used as controls. The results are shown in FIG. 15. A squalene production amount of the yeast expressing the mutated enzyme (K701_Mutant2), wherein the 6 amino acids were substituted, was significantly increased, compared to that of K701_tHMGR.

Mutated Enzyme (K701_Mutant:I773L)

```
                                          (SEQ ID NO: 37)
5'-ACGCATTGAAAAAATCATTTAACTCTA-3'

(SEQ ID NO: 38)
5'-ATTTTTTCAATGCGTTTTGTCCCTCTTC-3'
```

Example 10

In this Example, the procedure described in Example 5 was repeated using the K701_tHMGR expression vector obtained in Comparative Example 1 except that 2 amino acid mutations were introduced into amino acid residues in an Sα2 region instead of 3 amino acid mutations, and 2 amino acid mutations were introduced into amino acid residues in an Lα2 region instead of 3 amino acid mutations, to prepare a mutated enzyme and the amount of squalene production was examined. (The numbers for identifying the mutation position are same as those of Example 5.

That is to say, the amino acid substitution mutations were introduced into the K701_tHMGR expression vector, so that the amino acid sequence of an Sα2 region becomes "EEGQNALKKSFN" and the amino acid sequence from HMG-CoA binding site to an Lα2 region thereof becomes "DKKAASINWIN". That is, isoleucine (the 741 position) of the 7th position of an Sα2 region was substituted by leucine, and alanine (the 776 position) of the 10th position of an Sα2 region was substituted by serine. Further, proline (the 850 position) existed at the 2nd position from the amino terminus of an Lα2 region to an amino terminus of HMGR, which is just behind the HMG-CoA binding site, was substituted by alanine, alanine (the 852 position) of the 1st position of an Lα2 region was substituted by serine, isoleucine (the 856 position) of the 5th position of an Lα2 region was substituted by threonine, and glutamic acid (the 857 position) of the 6th position of an Lα2 region was substituted by asparagine.

Mutations were introduced by the above primers (SEQ ID NO: 23 to 29 and 37 to 38), and a revertant mutation was introduced by the following primers (SEQ ID NO: 39 to 40).

An introduction of the amino acid substitution mutations was carried out using the K701_tHMGR expression vector as a template. In accordance with the method of Comparative Example 3, the mutations were introduced in order by repeating the procedures using different primers, so that a vector, wherein the 5 amino acids were substituted, was constructed.

The constructed vector was introduced into the host, i.e. sake yeast so as to obtain a K701_Mutant3 strain. The enhancing effects of mevalonate pathways were compared by using an index as amounts of squalene productions of each strain. The amount of squalene production was measured in accordance with a method described in Example 2(2). A culture was carried out using a conical flask equipped with a baffle. Precultured yeast cells were added to a YPD medium (containing 5% glucose), and the whole was cultured at 28° C. while rotating at 250 rpm. After 2 days of culturing, the cultured yeast cells were collected, and the amount of squalene production was measured. In addition, the ADK4653_tHMGR and K701_tHMGR were used as controls. The results are shown in FIG. 16. A squalene production amount of the yeast expressing the mutated enzyme (K701_Mutant3), wherein the 5 amino acids were substituted, was significantly increased, compared to that of K701_tHMGR.

Mutated Enzyme (K701_Mutant:T856I)

```
                                          (SEQ ID NO: 39)
5'-AACTGGATCAATGGTCGTGGTAAGAGT-3'

(SEQ ID NO: 40)
5'-ACCATTGATCCAGTTGATAGAAGCGGC-3'
```

Example 11

In this Example, the procedure described in Example 5 was repeated using the K701_tHMGR expression vector obtained in Comparative Example 1 except that 2 amino acid mutations were introduced into amino acid residues in an Lα2 region instead of 3 amino acid mutations, to prepare a mutated enzyme and the amount of squalene production was examined. (The numbers for identifying the mutation position are same as those of Example 5.

That is to say, the amino acid substitution mutations were introduced into the K701_tHMGR expression vector, so that the amino acid sequence of an Sα2 region becomes "EEGQNLLKKSFN" and the amino acid sequence from HMG-CoA binding site to an Lα2 region thereof becomes "DKKAASINWIN". That is to say, alanine (the 772 position) of the 6th position of an Sα2 region was substituted by leucine, isoleucine (the 773 position) of the 7th position of an Sα2 region was substituted by leucine, and alanine (the 776 position) of the 10th position of an Sα2 region was substituted by serine. Further, proline (the 850 position) existed at the 2nd position from the amino terminus of an Lα2 region to an amino terminus of HMGR, which is just behind the HMG-CoA binding site, was substituted by alanine, alanine (the 852 position) of the 1st position of an Lα2 region was substituted by serine, and glutamic acid (the 857 position) of the 6th position of an Lα2 region was substituted by asparagine.

An introduction of the amino acid substitution mutations was carried out using the K701_tHMGR expression vector as a template. In accordance with the method of Comparative Example 3, the mutations were introduced in order by repeating the procedures using different primers, so that a vector, wherein the 6 amino acids were substituted, was constructed.

Mutations were introduced by the above primers (SEQ ID NO: 23 to 32), and a revertant mutation was introduced by the above primers (SEQ ID NO: 39 to 40) The constructed vector was introduced into the host, i.e. sake yeast so as to obtain a K701_Mutant4 strain. The enhancing effects of mevalonate pathways were compared by using an index as amounts of squalene productions of each strain. The amount of squalene production was measured in accordance with a method described in Example 2(2). A culture was carried out using a conical flask equipped with a baffle. Precultured yeast cells were added to a YPD medium (containing 5% glucose), and the whole was cultured at 28° C. while rotating at 250 rpm. After 2 days of culturing, the cultured yeast cells were collected, and the amount of squalene production was measured. In addition, the ADK4653_tHMGR and K701_tHMGR were used as controls. The results are shown in FIG. 16. A squalene production amount of the yeast expressing the mutated enzyme (K701_Mutant4), wherein the 6 amino acids were substituted, was significantly increased, compared to that of K701_tHMGR.

The amino acids of positions of (a) to (g) of vectors in Examples 3, and 5 to 11, and Comparative Examples 2 to 6 (amino acids substitutions form the ADK4653_tHMGR, or K701_tHMGR) and relative values of squalene production of Examples and Comparative Examples are summarized in Table 1. In connection to this, each amino acid is described with one letter.

TABLE 1

| | Mutation introduced tHMGR | (a) 10th in S α 2 region | (b) 1st from C terminal in DKK | (c) 1st in L α 2 region | (d) 6th in L α 2 region | (e) 7th in S α 2 region | (f) 5th in L α 2 region | (g) 6th in S α 2 region | Squalene production (relative value when production of ADK_tHMGR is 100) |
|---|---|---|---|---|---|---|---|---|---|
| Comparative Example 2 | K701_tHMGR | *A | *P | *A | *E | *I | *I | *A | 0.2 |
| Example 3 | ADK_tHMGR | S | A | S | N | L | T | L | 100.0 |
| Example 5 | K701_tHMGR | A → S | P → A | A → S | E → N | I → L | I → T | A → L | 92.1 |
| Example 6 | ADK_tHMGR | S | A | S | N | L | T → *I | L | 50.3 |
| Example 7 | ADK_tHMGR | S | A | S | N | L | T | L → *A | 54.2 |
| Example 8 | ADK_tHMGR | S | A | S | N | L → *I | T | L | 18.8 |
| Example 9 | K701_tHMGR | A → S | P → A | A → S | E → N | I → L | I → T | *A | 44.6 |
| Example 10 | K701_tHMGR | A → S | P → A | A → S | E → N | I → L | *I | *A | 18.2 |
| Example 11 | K701_tHMGR | A → S | P → A | A → S | E → N | I → L | *I | A → L | 22.8 |
| Comparative Example 3 | ADK_tHMGR | S | A | S → *A | N | L | T | L | 13.9 |
| Comparative Example 3 | ADK_tHMGR | S | A | S → *A | N | L | T → *I | L | 0.4 |
| Comparative Example 4 | ADK_tHMGR | S → *A | A | S | N | L | T | L | 0 |
| Comparative Example 5 | ADK_tHMGR | S | A → *P | S | N | L | T | L | 4.7 |
| Comparative Example 6 | ADK_tHMGR | S | A | S | N → *E | L | T | L | 0.3 |

* = amino acid of K701_tHMGR
(a) 10th in S α 2 region: 744th amino acid of ADK4653_tHMGR, 776th amino acid of K701_tHMGR
(b) 1st from C terminal in DKK: 818th amino acid of ADK4653_tHMGR, 850th amino acid of K701_tHMGR
(c) 1st in L α 2 region: 820th amino acid of ADK4653_tHMGR, 852nd amino acid of K701_tHMGR
(d) 6th in L α 2 region: 825th amino acid of ADK4653_tHMGR, 857th amino acid of K701_tHMGR
(e) 7th in S α 2 region: 741st amino acid of ADK4653_tHMGR, 773rd amino acid of K701_tHMGR
(f) 5th in L α 2 region: 824th amino acid of ADK4653_tHMGR, 856th amino acid of K701_tHMGR
(g) 6th in S α 2 region: 740th amino acid of ADK4653_tHMGR, 772nd amino acid of K701_tHMGR As is obvious from Comparative Example 2 and Example 3, ADK4653_tHMGR(a=S, b=A, c=S, d=N, e=L, f=T, g=L) wherein the 7 amino acids positioned in (a), (b), (c), (d), (e), (f), and (g) are different from those of K701_tHMGR(a=A, b=P, c=A, d=E, e=I, f=I, g=A), exhibited a significantly excellent squalene production amount. Further, as is obvious from Example 5, a relative value of a squalene production amount reached 92.1 similar to that of ADK4653_tHMGR by substituting the 7 amino acids positioned in (a), (b), (c), (d), (e), (0, and (g) of K701_tHMGR by the 7 amino acids of ADK4653_tHMGR. The ADK4653_tHMGR is different from the K701_tHMGR in the length of an amino acid sequence, and an identity of an amino acid sequence of truncated HMGR (tHMGR) therebetween is 78%. Thus, it is surprising that the amount of squalene production reaches the same level of ADK4653_tHMGR by substituting a mere 7 amino acids in the amino acids of K701_tHMGR by the amino acids of ADK4653_tHMGR. That is to say, it is considered that these 7 amino acids positioned in (a), (b), (c), (d), (e), (0, and (g) play an important role for the squalene production through hydroxymethylglutaryl CoA reductase.

Further, as is clear from the results of Comparative Examples 3 to 6, when any one of the amino acids positioned in (a), (b), (c), and (d) of ADK4653_tHMGR was substituted by an amino acid of K701_tHMGR, the relative values of a squalene production amount are dramatically decreased to 0-13.9. That is, it is considered that the amino acids positioned in (a), (b), (c), and (d) are particularly important for the production of squalene through hydroxymethylglutaryl CoA reductase.

Furthermore, as is clear from the results of Examples 6 to 11, when any one of the 3 amino acids positioned in (e), (f), and (g) is the amino acid of K701_tHMGR, relative values of a squalene production amount are 18.2 to 54.2. That is, compared to the amino acids positioned in (a), (b), (c), and (d), even if the amino acids positioned in (e), (f), and (g) were those of K701_tHMGR, the squalene production amount was high.

INDUSTRIAL APPLICABILITY

According to the present invention, in the production of a terpenoid compound, the production of mevalonic acid and the production of squalene can be increased. Thus, mevalonic acid and squalene obtainable by the present invention can be used, for example, as a material for producing drug medicine.

Although the present invention has been described with reference to specific embodiments, various changes and modifications obvious to those skilled in the art are possible without departing from the scope of the appended claims.

The invention claimed is:
1. A hydroxymethylglutaryl CoA, comprising:
   (a) an amino acid at the 10th position in an Sα2 amino acid sequence of HMGR is serine (S),
   (b) an amino acid at the 1st position from the carboxyl terminal in the DKK (aspartic acid-lysine-lysine) region of the HMG-CoA binding site of HMGR is alanine (A),
   (c) an amino acid at the 1st position in an Lα2 amino acid sequence of HMGR is serine (S), and
   (d) an amino acid at the 6th position in an Lα2 amino acid sequence of HMGR is asparagine (N),
   (e) an amino acid at the 7th position in an Sα2 amino acid sequence of HMGR is leucine (L),
   (f) an amino acid at the 5th position in an Lα2 amino acid sequence of HMGR is threonine (T), and
   (g) an amino acid at the 6th position in an Sα2 amino acid sequence of HMGR is leucine (L).
2. The hydroxymethylglutaryl CoA reductase according to claim 1, which does not comprise membrane-bound domain.
3. A polynucleotide encoding the hydroxymethylglutaryl CoA reductase according to claim 1.
4. A microorganism having the polynucleotide according to claim 3.
5. A vector having the polynucleotide according to claim 3.
6. A transformant having the vector according to claim 5.
7. A method for preparing terpenoid characterized in that the transformant according to claim 6 is cultured.

* * * * *

```
                         SEQUENCE LISTING

<160> NUMBER OF SEQ ID NOS: 40

<210> SEQ ID NO 1
<211> LENGTH: 1022
<212> TYPE: PRT
<213> ORGANISM: Saccharomycopsis fibuligera

<400> SEQUENCE: 1

Met Phe Ser Leu Ser Asn Tyr Val Ser Asn Trp Leu Ala Ser Leu Ala
1               5                   10                  15

Arg Leu Ser Ala His Lys Pro Ile His Val Ile Phe Leu Thr Thr Leu
            20                  25                  30

Leu Thr Ala Val Ala Tyr Leu Ser Val Val Asp Glu Tyr Leu Asn Phe
        35                  40                  45

Asp Ser Phe Asp Ile Ser Asn Val Ser Phe Tyr His Pro Pro Ser Ser
    50                  55                  60

Lys Asp Tyr Lys Asp Trp Thr Leu Ile Glu Asp Ala Ser Ala Tyr Pro
65                  70                  75                  80

Asn Ala Ala Arg Ile Ala Ile Thr Pro Leu Glu Phe Arg Arg Ile Ala
                85                  90                  95

Lys His Glu Ile Pro Ala Ile Ala Asn Thr Phe Tyr Gly Val Asp Ser
            100                 105                 110

Thr Glu Lys Tyr Leu Ile Ser Glu Tyr Glu Asn Ala Gln Asp Ser Ile
        115                 120                 125

Asp Ser Ile Arg Thr Val Val Ser Asn Asp Gly Thr Ala Trp Lys Ile
    130                 135                 140

Val His Gln Tyr Lys Thr Ser Lys Tyr Gln Glu Tyr Leu Lys Asn Ala
145                 150                 155                 160

Tyr Lys Thr Leu Gln Ser Val Ile Arg Gly Ala Glu Thr Tyr Asp Ile
                165                 170                 175

Ala Ile Ile Thr Ile Ala Tyr Ala Ala Met Tyr Tyr Thr Phe Phe Lys
            180                 185                 190

Leu Phe Tyr Asp Met Arg Thr Gln Ala Asn Ser Lys Phe Trp Leu Gly
        195                 200                 205

Phe Ala Ser Ala Ser Ser Leu Phe Ala Phe Leu Ala Val Gly
    210                 215                 220

Thr Ala Lys Ile Phe Asn Ile Arg Val Ser Leu Leu Ser Leu Ser Glu
225                 230                 235                 240

Gly Ile Pro Phe Leu Val Ala Thr Val Gly Phe Asn Arg Ile Val Lys
                245                 250                 255

Leu Ser Ala Ala Val Leu Asn Ala Ala Val Asp Lys Glu Ser His
            260                 265                 270

Ser Ile Ser Leu Leu Ile Tyr Arg Gln Leu Lys Asp Lys Ala Leu Asn
        275                 280                 285

Phe Val Lys Asp Gln Leu Leu Cys Ala Ala Ala Phe Val Gly Cys Ser
```

-continued

```
            290                 295                 300
Ile Tyr Ala Ser His Leu Glu Gly Leu Arg Ser Phe Cys Leu Leu Ser
305                 310                 315                 320
Ala Phe Ile Met Ile Tyr Asp Val Leu Leu Thr Tyr Ser Tyr Tyr Ser
                    325                 330                 335
Ala Val Leu Ala Leu Lys Val Glu Ile Asn Met Ile His Gln Ser Ile
                340                 345                 350
Ala Leu Lys Asp Ala Leu Glu Glu Asp Gly Ile Pro Glu Leu Ala Ala
            355                 360                 365
Arg Gln Ala Ser Leu Ala Ser Phe Gly Ser Gln Lys Glu Leu Ser Leu
        370                 375                 380
Gly Pro Asn Ser Gly Tyr Val Thr Ala Phe Lys Ile Ala Ser Val Ala
385                 390                 395                 400
Phe Phe Phe Ala Phe His Ala Tyr Leu Val Gly Ser Asn Trp Val Phe
                    405                 410                 415
Leu Ser Ser Asn Glu Asp Ile Ile Glu Gly His Asn Leu Ser Lys Ser
                420                 425                 430
Ile Ala Lys His Ile Ser Ile Gly Ser Thr Gly Thr Val Val Thr Leu
            435                 440                 445
Leu Glu Pro Lys Ile Tyr Val Pro Lys Asn Ile Leu Phe Gln Val Glu
        450                 455                 460
Asp Leu Val Ile Ser Ile Leu Glu Lys Leu Ser Thr Ala Ile Arg Asp
465                 470                 475                 480
Lys Phe Ile Ser Lys Thr Leu Leu Phe Phe Leu Gly Thr Ser Ser Ala
                    485                 490                 495
Ile Asn Val Tyr Leu Leu Asn Ala Ala Arg Ala His Ser Ile Asp Lys
                500                 505                 510
Pro Ser Gln Arg Leu Ser Lys Ala Ile Ala Ser Lys Glu Ala Ser Arg
            515                 520                 525
Arg Ala Lys Ala Ala Tyr Glu Ser Gln Lys Ser Val Ser Lys Ser Thr
        530                 535                 540
Asp Asp Thr Ala Ser Ser Glu Pro Thr Phe Asp Val Lys Asn Ile Leu
545                 550                 555                 560
Pro Asn Ser Gly Ile Glu His Thr Phe Glu Glu Leu Val Asp Ile Leu
                    565                 570                 575
Lys Asn Gly Glu Val Ser Ser Leu Ser Asn Glu Glu Val Thr Thr Leu
                580                 585                 590
Val Val Lys Asp Lys Leu Pro Leu Tyr Ala Leu Glu Lys Lys Leu Gly
            595                 600                 605
Asp Thr Thr Arg Ala Val Ala Val Arg Arg Gln Ala Ile Ser Lys Leu
        610                 615                 620
Ala Lys Ser Pro Ile Val Asp Ser Ser Ser Val Pro Tyr Leu Asn Tyr
625                 630                 635                 640
Asp Tyr Asp Lys Val Phe Gly Ala Cys Cys Glu Asn Val Ile Gly Tyr
                    645                 650                 655
Ile Pro Leu Pro Leu Gly Val Ala Gly Pro Leu Leu Ile Asp Gly Lys
                660                 665                 670
Pro Phe His Ile Pro Met Ala Thr Thr Glu Gly Cys Leu Val Ala Ser
            675                 680                 685
Thr Met Arg Gly Cys Lys Ala Ile Asn Ala Gly Gly Gly Val Ser Thr
        690                 695                 700
Val Leu Thr Arg Asp Gly Met Thr Arg Gly Pro Cys Val Lys Phe Pro
705                 710                 715                 720
```

```
Ser Leu Gln Arg Ala Gly Ala Cys Lys Ile Trp Leu Asp Ser Glu Glu
            725                 730                 735

Gly Gln Asn Leu Leu Lys Lys Ser Phe Asn Ser Thr Ser Arg Phe Ala
        740                 745                 750

Arg Leu Gln His Val Gln Thr Ala Ile Ala Gly Ser Leu Leu Phe Ile
    755                 760                 765

Arg Phe Arg Thr Thr Thr Gly Asp Ala Met Gly Met Asn Met Ile Ser
770                 775                 780

Lys Gly Val Glu Phe Thr Leu Lys Gln Met Val Glu Glu Tyr Gly Trp
785                 790                 795                 800

Ser Asp Met Asp Val Ile Ser Val Ser Gly Asn Tyr Cys Thr Asp Lys
                805                 810                 815

Lys Ala Ala Ser Ile Asn Trp Thr Asn Gly Arg Gly Lys Ser Ile Val
            820                 825                 830

Ala Glu Ala Arg Ile Pro Gly Glu Val Val Arg Lys Val Leu Lys Ser
        835                 840                 845

Asp Val Asp Ala Leu Val Glu Leu Asn Val Ser Lys Asn Leu Ile Gly
    850                 855                 860

Ser Ala Met Ala Gly Ser Ile Gly Gly Phe Asn Ala His Ala Ala Asn
865                 870                 875                 880

Leu Val Thr Ala Val Phe Leu Ala Cys Gly Gln Asp Pro Ala Gln Asn
                885                 890                 895

Val Glu Ser Ser Asn Cys Ile Thr Leu Ile Asp Asn Val Asp Gly Asp
            900                 905                 910

Leu Gln Ile Ser Val Ser Met Pro Ser Ile Glu Val Gly Thr Ile Gly
        915                 920                 925

Gly Gly Thr Ile Leu Glu Pro Gln Gly Ala Met Leu Asp Leu Leu Gly
    930                 935                 940

Val Arg Gly Pro His Pro Thr Thr Pro Gly Ala Asn Ala His Gln Leu
945                 950                 955                 960

Ala Lys Val Val Ala Ser Ala Val Leu Ala Ala Glu Leu Ser Leu Cys
                965                 970                 975

Ser Ala Leu Ala Ala Gly His Leu Val Gln Ser His Met Gln His Asn
            980                 985                 990

Arg Gly Lys Pro Ala Ala Pro Ala  Ala Ala Pro Ser Ser  Lys Ala Asp
        995                 1000                1005

Val Gln  Arg Leu Thr Asp Gly  Ser Lys Ile Cys Ile  Lys Ser
    1010                1015                1020

<210> SEQ ID NO 2
<211> LENGTH: 3069
<212> TYPE: DNA
<213> ORGANISM: Saccharomycopsis fibuligera

<400> SEQUENCE: 2
atgtttagcc ttagtaatta tgtgtccaat tggctcgcgt cattggcaag gttgtcggca      60
cacaaaccaa tccacgttat attcttaaca acgttgttaa ccgctgttgc ttacttgtct     120
gtcgtcgacg agtatctcaa ctttgactca ttcgatatct ccaatgtttc cttctatcat     180
cctccatctt caaaggacta taagattgg actttaattg aggatgctag tgcttatcca     240
aacgcagctc gtattgcaat cactccactt gagtttagaa gaattgctaa acatgaaatc     300
ccggctatag caaacacttt ttacggcgtc gactccaccg agaaatactt gatttctgag     360
tacgaaaatg cccaggacag cattgactca atcagaactg ttgtttccaa tgatgggact     420
```

```
gcttggaaga ttgttcacca gtacaagacc agcaaatatc aagaatacct caaaaatgct    480
tacaaaacct tacagtctgt tattcgtggt gctgaaactt atgatattgc tatcattaca    540
attgcctacg ctgccatgta ctacaccttt tttaagctct tttatgatat gagaacccaa    600
gccaactcca agttctggtt gggttttgct tcagcctcat catctctgtt tgcattttg     660 cttgctgttg aactgccaa atctttaat attagagttt ccttattgag cttgtctgaa      720
ggcattccat ttttggttgc cacggttgga ttcaacagaa ttgtaaagct ttccgccgct    780
gttttgaacg ccgctgcagt tgacaaagag tctcatagta tcagtttatt gatttataga    840
caacttaagg ataaagccct caattttgtc aaagatcaat tgttatgtgc tgctgcattt    900
gttgggtgct caatttatgc atcgcacttg aaggattga gaagcttttg tttattgagt     960
gcattcatca tgatttacga cgtgcttttg acttattcct actattctgc tgtcttggct   1020
cttaaagttg aaatcaacat gattcaccaa tctattgctc ttaaggatgc attagaagaa   1080
gacggtattc ctgaacttgc tgctagacaa gcttctttgg catcatttgg gtcacaaaaa   1140
gaacttagct tgggtccaaa cagcggatat gttaccgcat tcaaaattgc tagcgttgca   1200 ttttttcttcg cattccatgc ttacttagtg ggcagtaact gggttttctt gagcagcaat  1260
gaggacatta tcgaaggcca caacttgtcc aagtcgattg ctaaacatat ttctattgga   1320
tcaaccggta ctgttgtcac tttattggaa ccgaaaattt acgttccaaa gaacatttta   1380
tttcaagttg aagatcttgt tatcagtatt cttgaaaaat tgtctactgc tatcagagat   1440
aaatttatta gtaagacttt gcttttcttt ttgggtacca gttctgccat caatgtctac   1500
ttgttgaacg ctgctagagc ccactccatt gataagccat ctcaacgtct tagcaaggct   1560
attgcttcaa aagaagcatc tagaagagca aaagctgctt atgaatcaca aaagagtgtt   1620
tcaaagagca ccgatgatac tgctagtagc gagccaactt ttgacgtaaa gaatatattg   1680
ccaaatagtg gtattgaaca tacttttgaa gaattagttg acattctcaa gaatggcgaa   1740
gtttctagct tgtctaatga agaagttact acccttgttg ttaaagataa attgccatta   1800
tatgctcttg aaaagaagtt aggtgacact actcgtgctg ttgctgttcg tcgtcaagct   1860
atttccaaat tggccaaaag cccaattgtt gatagctcta gtgttccata cttgaattac   1920
gattatgata aggtgtttgg cgcatgttgt gaaaacgtca ttggttatat tccattgcct   1980
cttggtgttg ctggtccatt gttaattgat ggtaagccat ccatattcc aatggctact    2040 actgaaggtt gtcttgttgc ttctaccatg cgcggttgta aagctattaa tgctggtggc   2100
ggtgttagca ccgtcttgac tagagatggt atgacaagag gtccttgtgt taaattccca   2160
tctttgcaac gtgccggtgc ttgtaagatt tggttagatt ctgaagaagg tcaaaacttg   2220
ttgaaaaaat cattcaattc tacttctaga tttgctagat gcaacatgt tcaaactgcc    2280 attgctggtt ctttgctttt cattagattt agaactacta ctggtgatgc tatgggtatg   2340
aatatgattt ccaaaggtgt tgaatttaca ttgaaacaaa tggttgaaga atatggttgg   2400
tctgatatgg atgttatctc tgtttccggt aactactgta ctgataagaa agccgcttct   2460
attaactgga ccaatggtcg tggtaagagt attgttgctg aagctcgtat tcctggagaa   2520
gttgtcagaa aagttcttaa gagtgacgtt gatgctcttg ttgaattaaa cgtcagcaag   2580
aatttgattg gttctgcaat ggccggctct attggtggtt tcaatgctca tgctgcaaat   2640
ttggtcactg ctgttttctt agcctgcggt caagatcctg ctcaaaatgt tgaaagttcc   2700
aactgtatca ctttaattga taatgttgat ggcgatttgc aaatatccgt ttctatgcca   2760
```

```
tctattgaag ttggtactat tggtggtggt actattcttg aacctcaagg tgctatgctt    2820
gatttattgg gagttcgtgg tccacatcca actactccag gggctaatgc tcatcagctt    2880
gcaaaggttg ttgcttctgc tgttttggcc gctgaattat cattgtgttc agcattggct    2940
gctggtcatt tagttcaaag tcatatgcaa cataaccgtg gtaaacctgc tgctccagcg    3000
gccgctccat caagcaaggc tgatgttcag cgtttgactg atggatcaaa gatctgtatc    3060
aaatcttaa                                                            3069

<210> SEQ ID NO 3
<211> LENGTH: 41
<212> TYPE: DNA
<213> ORGANISM: Artificial Sequence
<220> FEATURE:
<223> OTHER INFORMATION: FL HMGR primer-1

<400> SEQUENCE: 3
aatcaactgg tacccgggat gtttagcctt agtaattatg t                        41

<210> SEQ ID NO 4
<211> LENGTH: 44
<212> TYPE: DNA
<213> ORGANISM: Artificial Sequence
<220> FEATURE:
<223> OTHER INFORMATION: FL HMGR primer-2

<400> SEQUENCE: 4
ttagttaacc tctagagctc ttaagatttg atacagatct ttga                     44

<210> SEQ ID NO 5
<211> LENGTH: 19
<212> TYPE: DNA
<213> ORGANISM: Artificial Sequence
<220> FEATURE:
<223> OTHER INFORMATION: HGMR seq primer-1

<400> SEQUENCE: 5
tctgcacaat atttcaagc                                                 19

<210> SEQ ID NO 6
<211> LENGTH: 24
<212> TYPE: DNA
<213> ORGANISM: Artificial Sequence
<220> FEATURE:
<223> OTHER INFORMATION: HGMR seq primer-2

<400> SEQUENCE: 6
ttcgttttaa aacctaagag tcac                                           24

<210> SEQ ID NO 7
<211> LENGTH: 45
<212> TYPE: DNA
<213> ORGANISM: Artificial Sequence
<220> FEATURE:
<223> OTHER INFORMATION: tHGMR primer-1

<400> SEQUENCE: 7
aatcaactgg tacccgggat gtctcaacgt cttagcaagg ctatt                    45

<210> SEQ ID NO 8
<211> LENGTH: 44
<212> TYPE: DNA
<213> ORGANISM: Artificial Sequence
<220> FEATURE:
<223> OTHER INFORMATION: tHGMR primer-1
```

<400> SEQUENCE: 8
ttagttaacc tctagagctc ttaagatttg atacagatct ttga                    44

<210> SEQ ID NO 9
<211> LENGTH: 39
<212> TYPE: DNA
<213> ORGANISM: Artificial Sequence
<220> FEATURE:
<223> OTHER INFORMATION: tHGMR primer-3

<400> SEQUENCE: 9
aatcaactgg tacccgggat ggaccaattg gtgaaaact                          39

<210> SEQ ID NO 10
<211> LENGTH: 35
<212> TYPE: DNA
<213> ORGANISM: Artificial Sequence
<220> FEATURE:
<223> OTHER INFORMATION: tHGMR primer-4

<400> SEQUENCE: 10
ttagttaacc tctagagctc ttaggattta atgca                              35

<210> SEQ ID NO 11
<211> LENGTH: 33
<212> TYPE: DNA
<213> ORGANISM: Artificial Sequence
<220> FEATURE:
<223> OTHER INFORMATION: S820A primer-1

<400> SEQUENCE: 11
gccattaact ggaccaatgg tcgtggtaag agt                                33

<210> SEQ ID NO 12
<211> LENGTH: 33
<212> TYPE: DNA
<213> ORGANISM: Artificial Sequence
<220> FEATURE:
<223> OTHER INFORMATION: S820A primer-2

<400> SEQUENCE: 12
ggtccagtta atggcagcgg ctttcttatc agt                                33

<210> SEQ ID NO 13
<211> LENGTH: 33
<212> TYPE: DNA
<213> ORGANISM: Artificial Sequence
<220> FEATURE:
<223> OTHER INFORMATION: T824I primer-1

<400> SEQUENCE: 13
tctattaact ggatcaatgg tcgtggtaag agt                                33

<210> SEQ ID NO 14
<211> LENGTH: 33
<212> TYPE: DNA
<213> ORGANISM: Artificial Sequence
<220> FEATURE:
<223> OTHER INFORMATION: T824I primer-2

<400> SEQUENCE: 14
gatccagtta atagaagcgg ctttcttatc agt                                33

<210> SEQ ID NO 15

```
<211> LENGTH: 33
<212> TYPE: DNA
<213> ORGANISM: Artificial Sequence
<220> FEATURE:
<223> OTHER INFORMATION: S820A/T824I primer-1

<400> SEQUENCE: 15
gccattaact ggatcaatgg tcgtggtaag agt                               33

<210> SEQ ID NO 16
<211> LENGTH: 33
<212> TYPE: DNA
<213> ORGANISM: Artificial Sequence
<220> FEATURE:
<223> OTHER INFORMATION: S820A/T824I primer-2

<400> SEQUENCE: 16
gatccagtta atggcagcgg ctttcttatc agt                               33

<210> SEQ ID NO 17
<211> LENGTH: 27
<212> TYPE: DNA
<213> ORGANISM: Artificial Sequence
<220> FEATURE:
<223> OTHER INFORMATION: S744A primer-1

<400> SEQUENCE: 17 tgaaaaagc tttcaattct acttcta                                       27

<210> SEQ ID NO 18
<211> LENGTH: 27
<212> TYPE: DNA
<213> ORGANISM: Artificial Sequence
<220> FEATURE:
<223> OTHER INFORMATION: S744A primer-2

<400> SEQUENCE: 18
attgaaagct tttttcaaca agttttg                                      27

<210> SEQ ID NO 19
<211> LENGTH: 27
<212> TYPE: DNA
<213> ORGANISM: Artificial Sequence
<220> FEATURE:
<223> OTHER INFORMATION: A818P primer-1

<400> SEQUENCE: 19
tgataagaaa ccagcttcta ttaactg                                      27

<210> SEQ ID NO 20
<211> LENGTH: 27
<212> TYPE: DNA
<213> ORGANISM: Artificial Sequence
<220> FEATURE:
<223> OTHER INFORMATION: A818P primer-2

<400> SEQUENCE: 20
gctggtttct tatcagtaca gtagtta                                      27

<210> SEQ ID NO 21
<211> LENGTH: 28
<212> TYPE: DNA
<213> ORGANISM: Artificial Sequence
<220> FEATURE:
<223> OTHER INFORMATION: N825E primer-1

<400> SEQUENCE: 21
```
tggaccgaag gtcgtggtaa gagtattg                                      28

<210> SEQ ID NO 22
<211> LENGTH: 28
<212> TYPE: DNA
<213> ORGANISM: Artificial Sequence
<220> FEATURE:
<223> OTHER INFORMATION: N825E primer-2

<400> SEQUENCE: 22
acgaccttcg gtccagttaa tagaagcg                                      28

<210> SEQ ID NO 23
<211> LENGTH: 33
<212> TYPE: DNA
<213> ORGANISM: Artificial Sequence
<220> FEATURE:
<223> OTHER INFORMATION: A852S-I856T primer-1

<400> SEQUENCE: 23
tctatcaact ggaccgaagg tcgtggtaag agt                                33

<210> SEQ ID NO 24
<211> LENGTH: 33
<212> TYPE: DNA
<213> ORGANISM: Artificial Sequence
<220> FEATURE:
<223> OTHER INFORMATION: A852S-I856T primer-2

<400> SEQUENCE: 24
ggtccagttg atagaagctg gtttttttgtc ggt                               33

<210> SEQ ID NO 25
<211> LENGTH: 27
<212> TYPE: DNA
<213> ORGANISM: Artificial Sequence
<220> FEATURE:
<223> OTHER INFORMATION: A776S primer-1

<400> SEQUENCE: 25
aaaaaatcat ttaactctac atcaaga                                       27

<210> SEQ ID NO 26
<211> LENGTH: 28
<212> TYPE: DNA
<213> ORGANISM: Artificial Sequence
<220> FEATURE:
<223> OTHER INFORMATION: A776S primer-2

<400> SEQUENCE: 26
gttaaatgat tttttaattt gcgttttg                                      28

<210> SEQ ID NO 27
<211> LENGTH: 27
<212> TYPE: DNA
<213> ORGANISM: Artificial Sequence
<220> FEATURE:
<223> OTHER INFORMATION: E857N primer-1

<400> SEQUENCE: 27
tggaccaatg gtcgtggtaa gagtgtc                                       27

<210> SEQ ID NO 28
<211> LENGTH: 27
<212> TYPE: DNA

```
<213> ORGANISM: Artificial Sequence
<220> FEATURE:
<223> OTHER INFORMATION: E857N primer-2

<400> SEQUENCE: 28
acgaccattg gtccagttga tagaagc                                    27

<210> SEQ ID NO 29
<211> LENGTH: 27
<212> TYPE: DNA
<213> ORGANISM: Artificial Sequence
<220> FEATURE:
<223> OTHER INFORMATION: P850A primer-1

<400> SEQUENCE: 29
cgacaaaaaa gccgcttcta tcaactg                                    27

<210> SEQ ID NO 30
<211> LENGTH: 27
<212> TYPE: DNA
<213> ORGANISM: Artificial Sequence
<220> FEATURE:
<223> OTHER INFORMATION: P850A primer-2

<400> SEQUENCE: 30
gcggcttttt tgtcggtaca gtagtta                                    27

<210> SEQ ID NO 31
<211> LENGTH: 28
<212> TYPE: DNA
<213> ORGANISM: Artificial Sequence
<220> FEATURE:
<223> OTHER INFORMATION: A772L-I773L primer-1

<400> SEQUENCE: 31
aaaacttgtt gaaaaatca tttaactc                                    28

<210> SEQ ID NO 32
<211> LENGTH: 27
<212> TYPE: DNA
<213> ORGANISM: Artificial Sequence
<220> FEATURE:
<223> OTHER INFORMATION: A772L-I773L primer-2

<400> SEQUENCE: 32
ttttcaacaa gttttgtccc tcttctg                                    27

<210> SEQ ID NO 33
<211> LENGTH: 28
<212> TYPE: DNA
<213> ORGANISM: Artificial Sequence
<220> FEATURE:
<223> OTHER INFORMATION: L740A primer-1

<400> SEQUENCE: 33
aaaacgcatt gaaaaaatca ttcaattc                                   28

<210> SEQ ID NO 34
<211> LENGTH: 29
<212> TYPE: DNA
<213> ORGANISM: Artificial Sequence
<220> FEATURE:
<223> OTHER INFORMATION: L740A primer-2

<400> SEQUENCE: 34
ttttcaatgc gttttgacct tcttcagta                                  29
```

```
<210> SEQ ID NO 35
<211> LENGTH: 27
<212> TYPE: DNA
<213> ORGANISM: Artificial Sequence
<220> FEATURE:
<223> OTHER INFORMATION: L741I primer-1

<400> SEQUENCE: 35
acttgattaa aaaatcattc aattcta                                           27

<210> SEQ ID NO 36
<211> LENGTH: 29
<212> TYPE: DNA
<213> ORGANISM: Artificial Sequence
<220> FEATURE:
<223> OTHER INFORMATION: L741I primer-2

<400> SEQUENCE: 36 atttttaat caagttttga ccttcttca                                          29

<210> SEQ ID NO 37
<211> LENGTH: 27
<212> TYPE: DNA
<213> ORGANISM: Artificial Sequence
<220> FEATURE:
<223> OTHER INFORMATION: L773L primer-1

<400> SEQUENCE: 37
acgcattgaa aaaatcattt aactcta                                           27

<210> SEQ ID NO 38
<211> LENGTH: 28
<212> TYPE: DNA
<213> ORGANISM: Artificial Sequence
<220> FEATURE:
<223> OTHER INFORMATION: L773L primer-2

<400> SEQUENCE: 38
attttttcaa tgcgttttgt ccctcttc                                          28

<210> SEQ ID NO 39
<211> LENGTH: 27
<212> TYPE: DNA
<213> ORGANISM: Artificial Sequence
<220> FEATURE:
<223> OTHER INFORMATION: T856I primer-1

<400> SEQUENCE: 39
aactggatca atggtcgtgg taagagt                                           27

<210> SEQ ID NO 40
<211> LENGTH: 27
<212> TYPE: DNA
<213> ORGANISM: Artificial Sequence
<220> FEATURE:
<223> OTHER INFORMATION: T856I primer-2

<400> SEQUENCE: 40
accattgatc cagttgatag aagcggc                                           27
```

UNITED STATES PATENT AND TRADEMARK OFFICE
CERTIFICATE OF CORRECTION

PATENT NO. : 10,280,406 B2  
APPLICATION NO. : 15/302903  
DATED : May 7, 2019  
INVENTOR(S) : Takehanna et al.

Page 1 of 1

It is certified that error appears in the above-identified patent and that said Letters Patent is hereby corrected as shown below:

In the Claims

Column 51, Line 2: Claim 1, Delete "CoA, comprising:" and insert -- CoA reductase, comprising: --

Signed and Sealed this  
Ninth Day of July, 2019

Andrei Iancu  
*Director of the United States Patent and Trademark Office*